(12) United States Patent
Zang et al.

(10) Patent No.: US 11,022,592 B2
(45) Date of Patent: Jun. 1, 2021

(54) CHEMICAL SELF-DOPING OF ONE-DIMENSIONAL ORGANIC NANOMATERIALS FOR HIGH CONDUCTIVITY APPLICATION IN CHEMIRESISTIVE SENSING GAS OR VAPOR

(71) Applicant: University of Utah Research Foundation, Salt Lake City, UT (US)

(72) Inventors: Ling Zang, Salt Lake City, UT (US); Na Wu, Salt Lake City, UT (US); Paul Slattum, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 625 days.

(21) Appl. No.: 15/368,276

(22) Filed: Dec. 2, 2016

(65) Prior Publication Data
US 2017/0160252 A1 Jun. 8, 2017

Related U.S. Application Data

(60) Provisional application No. 62/373,750, filed on Aug. 11, 2016, provisional application No. 62/386,489, filed on Dec. 2, 2015.

(51) Int. Cl.
*G01N 27/12* (2006.01)
*C07D 471/06* (2006.01)
(Continued)

(52) U.S. Cl.
CPC ....... *G01N 33/0057* (2013.01); *C07D 471/06* (2013.01); *C09B 5/62* (2013.01);
(Continued)

(58) Field of Classification Search
CPC .... G01N 27/04; G01N 27/041; G01N 27/043; G01N 27/125; G01N 27/127; C07D 471/06; C09B 5/62
See application file for complete search history.

(56) References Cited

U.S. PATENT DOCUMENTS 6,409,816 B1 * 6/2002 Weber ................. C09B 67/0033
106/493
8,058,075 B2    11/2011 Zang et al.
(Continued)

FOREIGN PATENT DOCUMENTS

CN    103193775 A        7/2013
CN    104028308 A  *     9/2014
(Continued)

OTHER PUBLICATIONS

Boobalan, G. et al. "Self-assembly and optical properties of N N'-bis(4-(1-benzylpiperidine))perylene-3,4,9,10-tetracarboxylic diimide," Supramolecular Chemistry vol. 24, 2012, Issue 4, pp. 238-246. (Year: 2012).*

(Continued)

*Primary Examiner* — Christopher Adam Hixson
*Assistant Examiner* — Michelle Adams
(74) *Attorney, Agent, or Firm* — Thorpe North & Western, LLP.

(57) ABSTRACT

A chemiresistive vapor sensor compound for detecting target vapors can comprise a perylene-tetracarboxylic diimide (PTCDI) core according to structure (I):

(Continued)

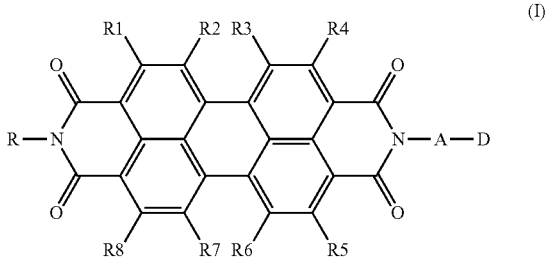

where R can be a morphology control group or -A'-D', A and A' can be independently a linking group, D and D' can be independently a strong electron donor which transfers electrons to the PTCDI core sufficient to form an anionic PTCDI radical of the PTCDI core, and R1 to R8 can be independently a side group. A chemiresistive vapor sensor for detection of a target compound can comprise an assembly of nanofibers formed of the chemiresistive sensor compound and a pair of electrodes operatively oriented about the assembly of nanofibers to allow electrical current to pass from a first electrode in the pair of electrodes through the assembly of nanofibers and to a second electrode in the pair of electrodes.

5 Claims, 21 Drawing Sheets

(51) Int. Cl.
  *G01N 33/00* (2006.01)
  *C09B 5/62* (2006.01)
  *G01N 27/04* (2006.01)
(52) U.S. Cl.
  CPC .......... *G01N 27/04* (2013.01); *G01N 27/127* (2013.01); *G01N 33/0037* (2013.01)

(56) References Cited

U.S. PATENT DOCUMENTS

| 8,486,708 | B2 | 7/2013 | Zang et al. |
| 8,889,420 | B2 | 11/2014 | Zang et al. |
| 2002/0107258 | A1* | 8/2002 | Kerwin ............... C07D 277/64 514/279 |
| 2008/0035914 | A1 | 2/2008 | Konemann et al. |
| 2009/0001354 | A1 | 1/2009 | Shukla et al. |
| 2012/0186648 | A1 | 7/2012 | Zang et al. |
| 2013/0065319 | A1 | 3/2013 | Zang et al. |
| 2014/0024171 | A1 | 1/2014 | Funahashi et al. |
| 2014/0083500 | A1 | 3/2014 | Mougnier et al. |
| 2014/0235493 | A1 | 8/2014 | Zang et al. |
| 2015/0243869 | A1* | 8/2015 | Segalman ............... H01L 35/24 136/203 |

FOREIGN PATENT DOCUMENTS

| JP | 2015127709 A | 7/2015 |
| WO | WO 2013095730 A2 | 6/2013 |
| WO | WO 2013/142886 A1 | 10/2013 |

OTHER PUBLICATIONS

SciFinder entry for CN-104028308-A with illustration of selected substances, accessed on Mar. 30, 2020. (Year: 2020).*
Balakrishnan et al, "Nanobelt Self-Assembly From an Organic N-Type Semiconductor: Propoxyethyl-PTCDI." JACS Communications; American Chemcal Society; Jul. 12, 2005; vol. 127 Issue 30; pp. 10496-10497.
Balakrishnan et al, "Effect of Side-Chain Substituents on Self-Assembly of Perylene Diimide Molecules: Morphology Control." JACS Articles; American Chemical Society; May 11, 2006; vol. 128 Issue 22; pp. 7390-7398.
Che et al, "Ultralong Nanobelts Self-Assembled From an Asymmetric Perylene Tetracarboxylic Diimide." JACS Communications; American Chemical Society; May 17, 2007; vol. 129 Issue 23; pp. 7234-7235.
Che et al, "Enhancing One-Dimensional Charge Transport Through Intermolecular π-Electron Delocalization: Conductivity Improvement for Organic Nanobelts." JACS Communications; American Chemical Society; Apr. 28, 2007; vol. 129 Issue 20; pp. 6354-6355.
Che et al, "Ultraselective Fluorescent Sensing of $Hg^{2+}$ Through Metal Coordination-Induced Molecular Aggregation." Chemical Communications; The Royal Society of Chemistry; Jan. 29, 2008; Issue 28; pp. 1413-1415.
Che et al, "Highly Polarized and Self-Waveguided Emission From Single-Crystalline Organic Nanobelts." Chemistry of Materials; American Chemical Society; May 11, 2009; vol. 21 Issue 13; pp. 2930-2934.
Chen et al, "Substitutional n-Type Doping of an Organic Semiconductor Investigation by Electron Paramagnetic Resonance Spectroscopy." The Journal of Physical Chemistry B; American Chemical Society; Oct. 15, 2004; vol. 108 Issue 45; pp. 17329-17336.
Datar et al, "Linearly Polarized Emission of an Organic Semiconductor Nanobelt." J. Phys. Chem B; American Chemical Society; Jun. 2, 2006; vol. 110 Issue 25; pp. 12327-12332.
Datar et al, "Surface-Assisted One-Dimensinoal Self-Assembly of a Perylene Based Semiconductor Molecule." Chemical Communications; Royal Society of Chemistry; Mar. 16, 2016; Issue 15; pp. 1649-1651.
Datar et al, "One-Dimensional Self-Assembly of a Water Soluble Perylene Diimide Molecule by pH Triggered Hydrogelation." Chemical Communications; Royal Science of Chemistry; Jun. 10, 2013; vol. 49 Issue 61; pp. 6894-6896.
Gregg et al, "Coulomb Forces and Doping in Organic Semiconductors." Chemistry of Materials; American Chemical Society; Jul. 13, 2004; vol. 16 Issue 23; pp. 4586-4599.
Hu et al, "Self-Assembled Sugar-Substituted Perylene Diimide Nanostructures With Homochirality and High Gas Sensitivity." Advanced Fuctional Materials; Material Views; Jun. 14, 2012; vol. 22 Issue 19; pp. 4149-4158.
Huang et al, "Ammonia Sensory Properties Based on Single-Crystalline Micro/Nanostructures of Perylenediimide Derivatives: Core-Substituted Effect." The Journal of Physical Chenmistry; American Chemical Society; May 5, 2011; vol. 115 Issue 21; pp. 10399-10404.
Huang et al, "Morphology Control of Nanofibril Donor-Acceptor Heterojunction to Achieve High Photoconductivity: Exploration of New Molecular Design Rule." American Chemical Society; Oct. 4, 2013; vol. 135 Issue 44; pp. 16490-16496.
Huang et al, "Effect of Core-Substituted Groups on Sensing Properties Based on Single Micro/Nanorod of Perylenediimide Derivatives." Sensors and Actuators B: Chemical; Elsevier; Nov. 2013; vol. 188; pp. 411-416.
Huang et al, "Probing the Sensory Property of Perylenediimide Derivatives in Hydrazine Gas: Core-Substituted Aromatic Group Effect." Applied Materials & Interfaces; American Chemical Society; Jun. 4, 2014; vol. 6 Issue 12; pp. 9307-9313.
Khopkar et al, "Perylenetracarboxylic Diimide (PTCDI) Nanowires for Sensing Ethyl Acetate in Wine." Journal of Nanoscience and Nanotechnology; American Scientific Publishers; Sep. 2014; vol. 14 Issue 9; pp. 6786-6788.
Kobayashi et al, "Hydrogen-Bonding-Assisted Self-Doping in Tetrathiafulvalene (TFF) Conductor." Journal of the Chemical Society; American Chemical Society; Jul. 1, 2009; vol. 131 Issue 29; pp. 9995-10002.
Li et al, "Controlling Charge Transport in Single Molecules Using Electrochemical Gate." Faraday Disscussions; Sep. 8, 2005; vol. 131; pp. 111-120.
Li et al, "Thermally Activated Electron Transport in single Redox Molecules." JACS Articles; American Chemical Society; Aug. 25, 2007; vol. 129 Issue 37; pp. 11535-11542.

(56) References Cited

OTHER PUBLICATIONS

Lei et al, "Highly Stable Blue Light-Emitting Materials With a Three-Dimensional Architecture: Improvement of Charge Injection and Electroluminescence Performance." New Journal of Chemisty; Royal Society of Chemistry; Feb. 10, 2010; vol. 34 Issue 4; pp. 699-707.

Liu et al, "Self-Organizing Liquid Crystal Perylene Diimide Thin Films: Spectroscopy, Crystallinity, and Molecular Orientation." The Journal of Physical Chemistry B; American Chemical Society; Jan. 9, 2002; vol. 106 Issue 6; pp. 1307-1315.

Malinauskas, "Self-Doped Polyanilines." Journal of Power Sources; Elsevier; Feb. 16, 2004; vol. 126 Issues 1-2; pp. 214-220.

Walzer et al, "Highly Efficient Organic Devices Based on Electrically Doped Transport Layers." Chemical Reviews; American Chemical Society; Mar. 27, 2007; vol. 107 Issue 4; pp. 1233-1271.

Yue et al, "Synthesis of Self-Doped Conducting Polyaniline." Journal of the American Chemical Society; American Chemical Society; Mar. 1990; vol. 112 Issue 7; pp. 2800-2801.

Zang et al, "One-Dimensional Self-Assembly of Planar π-Conjugated Molecules: Adaptable Building Blocks for Organic Nanodevices." Accounts of Chemical Research; American Chemical Society; Jul. 11, 2008; vol. 41 Issue 12; pp. 1596-1608.

Che et al.; "Ultrathin n-Type Organic Nanoribbons with High Photoconductivity and Application in Optoelectronic Vapor Sensing of Explosives;" Journal of American Chemical Society; (2010); pp. 5743-5750; vol. 132; <doi: 10.1021/ja909797q >.

Gregg et al.; "Doping Molecular Semiconductors: n-Type Doping of a Liquid Crystal Perylene Diimide;" Journal of American Chemical Society; (2001); pp. 7959-7960; vol. 123; <doi: 10.1021/ja016410k >.

Supplementary European Search Report dated Jul. 11, 2019, in EP Application No. 16890884.6, filed Dec. 2, 2016; 7 pages.

Chen et al.; "Self-Assembly of Perylene Imide Molecules into 1D Nanostructures: Methods, Morphologies, and Applications;" Chemical Reviews; (Oct. 6, 2015); pp. 11967-11998; vol. 115; <doi: 10.1021/acs.chemrev.5b00312 >.

Wang et al.; "Interfacial Donor-Acceptor Nanofibril Composites for Selective Alkane Vapor Detection;" ACS Sensors; American Chemical Society; (Mar. 9, 2016); 10 pages; vol. 1, Issue 5; <doi: 10.1021/acssensors.6b00018 >.

\* cited by examiner

CHEMICAL SELF-DOPING OF ONE-DIMENSIONAL ORGANIC NANOMATERIALS FOR HIGH CONDUCTIVITY APPLICATION IN CHEMIRESISTIVE SENSING GAS OR VAPOR

RELATED APPLICATION(S)

This application claims the benefit of U.S. Provisional Application No. 62/373,750, filed Aug. 11, 2016, and U.S. Provisional Application No. 62/386,489, filed Dec. 2, 2015, each of which is incorporated herein by reference.

GOVERNMENT INTEREST

This invention was made with government support under 2009-ST-108-LR0005 awarded by the U.S. Department of Homeland Security and grant CHE0931466 and grant CBET1502433 awarded by the National Science Foundation. The government has certain rights in the invention.

FIELD OF THE INVENTION

This invention relates to the field of vapor or gas detection using compounds based on perylene-tetracarboxylic diimide. Accordingly, the invention involves the fields of organic chemistry, chemical engineering, and nanotechnology.

BACKGROUND

Peroxide explosives, including TATP, DADP, and HMTD, represent one class of the most elusive explosives that can be easily made at home from commercially available products. The ease of preparation, together with the tremendous explosive power and easy initiation makes peroxide explosives preferred by terrorists and insurgents in making improvised explosive devices (IEDs) IEDs are one of the three major types of explosives of particular interest to the United States Department of Homeland Security. Current technologies cannot detect all required explosives with the speed, specificity, and distance demanded by checkpoint security. Furthermore, current detection systems are expensive. Therefore, it is emergent to develop an inexpensive but efficient method for peroxide explosive detection. $H_2O_2$ is commonly used as the chemical marker of peroxide explosives, which is often leaked from organic peroxides as a synthetic impurity, or can be produced from the chemical decomposition of peroxide explosives. Therefore, a sensory material with high sensitivity and selectivity to $H_2O_2$ would be beneficial for peroxide explosive detection. The development of a low-power sensor device that could provide inexpensive and simple peroxide detection could replace the current expensive explosive detection equipment with dependable and affordable sensors.

Most oxidant gases or vapors are hazardous chemicals, which need to be controlled and monitored. $H_2O_2$ is an industrial chemical widely used in applications such as waste water processing, paper manufacturing, bleaching, toothpaste, and hair color. $H_2O_2$ can be toxic if ingested, inhaled, or by contact with the skin or eyes. Inhalation of household strength $H_2O_2$ (3%) can cause respiratory irritation. Exposure to household strength $H_2O_2$ can cause mild ocular irritation. $NO_2$ is a well-known oxidant gas, which is produced from fossil fuel combustion processes, and is one of the most dangerous air pollutants. $NO_2$ plays a major role in the formation of ozone and acid rain. Continued or frequent exposure to $NO_2$ at higher than air quality standard may cause increased incidence of acute respiratory illness. A high efficiency, small, light, and low-power oxidant vapor sensor for real-time monitoring of hazardous oxidant gas would be advantageous.

SUMMARY

A chemiresistive vapor sensor compound for detecting target vapors can comprise a perylene-tetracarboxylic diimide (PTCDI) core according to structure (I):

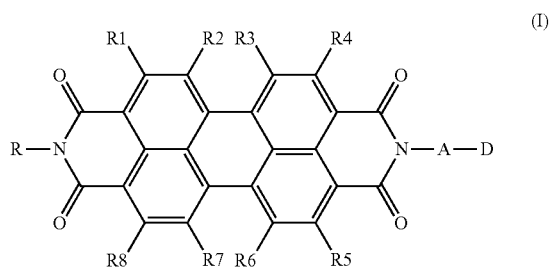

where R can be a morphology control group or -A'-D', A and A' can be independently a linking group, D and D' can be independently a strong electron donor which transfers electrons to the PTCDI core sufficient to form an anionic PTCDI radical of the PTCDI core, and R1 to R8 can be independently a side group.

A chemiresistive vapor sensor for detection of a target compound can comprise an assembly of nanofibers formed of the chemiresistive sensor compound and a pair of electrodes operatively oriented about the assembly of nanofibers to allow electrical current to pass from a first electrode in the pair of electrodes through the assembly of nanofibers and to a second electrode in the pair of electrodes.

In one aspect, a method of detecting target compounds can comprise exposing the assembly of nanofibers to a suspected target compound source, measuring an electrical response of the assembly of nanofibers, and displaying a detection metric based on the electrical response.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

Figure 1:
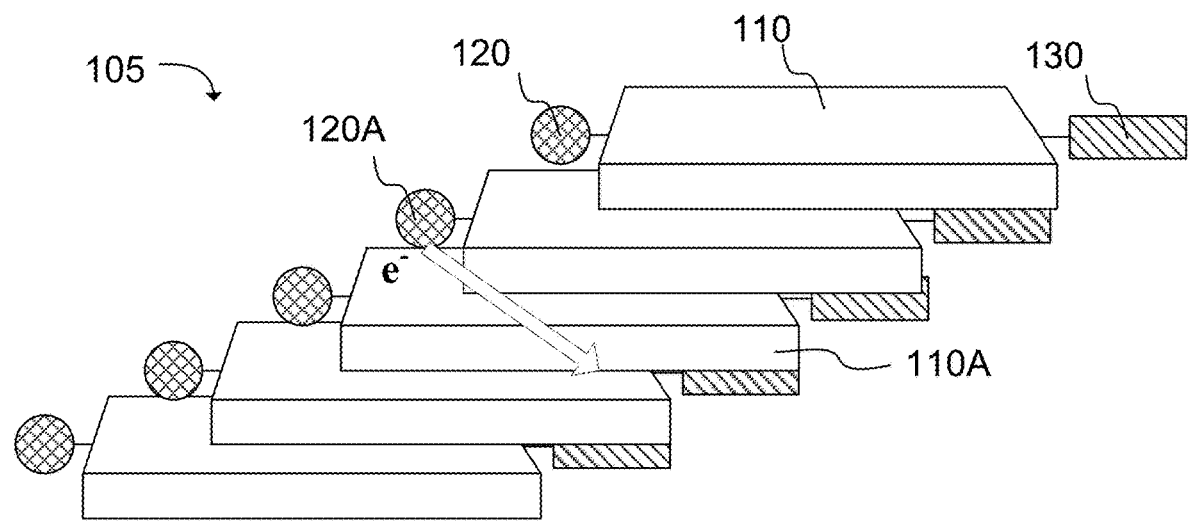
FIG. 1 is a schematic illustration of the conductivity enhancement of a PTCDI nanoribbon, in accordance with some examples of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a nanoribbon" includes reference to one or more of such materials and reference to "contacting" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of" For example, "at least one of A, B and C" explicitly includes only A, only B, only C, and combinations of each (e.g. A+B, B+C, A+C, and A+B+C).

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

An initial overview of technology embodiments is provided below and specific technology embodiments are then described in further detail. This initial summary is intended to aid readers in understanding the technology more quickly, but is not intended to identify key or essential features of the technology, nor is it intended to limit the scope of the claimed subject matter.

Highly conductive ultrathin nanoribbons can be fabricated from an amphiphilic electron donor-acceptor supramolecule perylene tetracarboxylic diimide (PTCDI) as the backbone scaffold to enable one-dimensional intermolecular assembly via strong π-stacking. The high conductivity results from a strong donor group-substituted PTCDI, of which the strong electron donor can form a charge transfer complex with the PTCDI moiety (acting as the acceptor) of an adjacent stacked molecule, generating an anionic radical of PTCDI. Upon self-assembling into 1D nanostructures, the electron generated is delocalized along the long axis of PTCDIs through the columnar π-stacking. The resultant PTCDI radicals function as n-type dopants located in the lattice of PTCDI crystals. The self-doped one-dimensional PTCDI nanomaterial has high conductivity, combined with n-type semiconductor character, and thus makes effective chemiresistive sensors for the detection of target vapors such as oxidant gases or vapors.

A chemiresistive vapor sensor compound for detecting vapor can include a perylene-tetracarboxylic diimide (PTCDI) core according to structure (I):

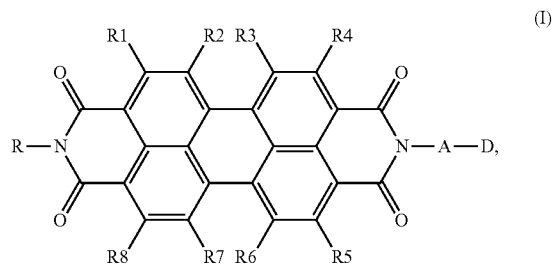

where R can be a morphology control group or -A'-D', A and A' can be independently a linking group, D and D' can be independently a strong electron donor which transfers electrons to the PTCDI core sufficient to form an anionic PTCDI radical of the PTCDI core, and R1 to R8 can be independently a side group.

The chemiresistive vapor sensor compound can be used with a chemiresistive vapor sensor for detection of a target compound. The sensor can include an assembly of nanofibers formed of the chemiresistive sensor compound and a pair of electrodes operatively oriented about the assembly of nanofibers to allow electrical current to pass from a first electrode in the pair of electrodes through the assembly of nanofibers and to a second electrode in the pair of electrodes.

Further, the chemiresistive vapor sensor can be used in a method of detecting target compounds. The method can include exposing the assembly of nanofibers to a suspected target compound source, measuring an electrical response of the assembly of nanofibers, and displaying a detection metric based on the electrical response.

It is noted that when discussing the chemiresistive vapor sensor compound, the chemiresistive vapor sensor, and the method of detecting target compounds, each of these respective discussions can be considered applicable to each of these examples, whether or not they are explicitly discussed in the context of that example. Thus, for example, in discussing details about the chemiresistive vapor sensor compound per se, such discussion also refers to the chemiresistive vapor sensor and the method of detecting target compounds, and vice versa.

With this overview in mind, the PTCDI core of the chemiresistive vapor sensor compound can include a variety of functional groups attached thereto. For example, side groups R1-R8 of the PTCDI core can typically be solubility enhancing groups, or other suitable groups that do not significantly affect the electrical properties of the PTCDI core. In some specific examples, R1-R8 can be independently selected from hydrogen, $C_1$-$C_8$ alkyl groups that do not significantly affect the electrical properties of the PTCDI core, or a combination thereof.

Further, in some cases R can be a morphology control group. Where this is the case, the morphology control group can typically be any group that does not impair the selectivity and function of the electron donor group. In some examples, the morphology control group can be a straight chain alkyl group (e.g. a $C_2$ to $C_{18}$ straight chain alkyl group). In one aspect, the morphology control group can be octyl, nonyl, decyl, undecyl, dodecyl, tridecyl, tetradecyl, pentadecyl, or hexadecyl.

In some other examples, the morphology control group can be a branched $C_8$-$C_{50}$ alkyl group. In some examples, the morphology control group R group can have a structure according to structure (II):

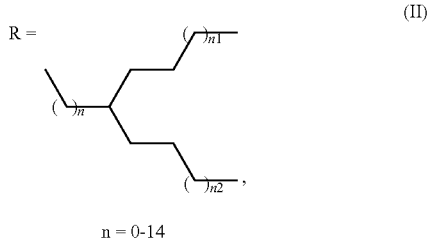

n = 0-14 where n1 and n2 are 0-14. In some specific examples, the morphology control group can be hexaheptyl, pentylhexyl, butylpentyl, or butyloctyl. Depending on the morphology control group employed, the chemirestistive sensor compound can have a morphology of a nanobelt, nanotubes, nanofibers, nanoribbon, or the like.

In some other examples, R is not a morphology control group. For example, in some cases, R can be -A'-D' to give the PTCDI core a structure according to structure (III):

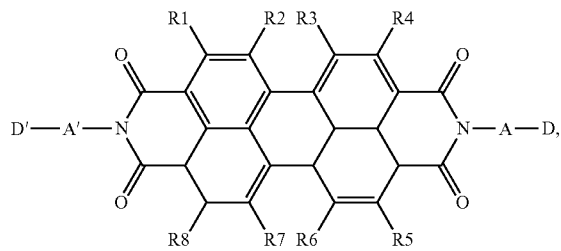

where A' can be a linking group and D' can be a strong electron donor group. It is noted that where R is -A'-D', A' can be the same linking group as A or a linking group that is different than A. Similarly, D' can be the same electron donor group as D or an electron donor group that is different from D.

Further, A and A' can generally be a carbon-based linking group. In one embodiment, A and A' can include at least one of $C_1$-$C_8$ alkylene groups, $C_3$-$C_8$ cycloalkylene groups, or phenylene groups. Although lengths can vary, A and A' can often be 0.8 nm to 2 nm or alternatively 5 to 12 carbons in length measured by carbon-carbon single bond length. In some cases, the carbon-based linking group of A and A' can include oxygen, nitrogen, and/or sulfur substitutions. For example, ether, ester or amide linkages can serve as linker groups. Non-limiting examples of substituted linking groups can include

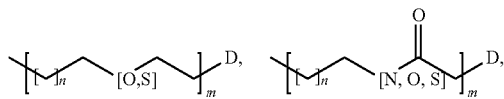

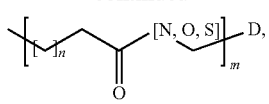

or the like, where n can be an integer from 0 to 10 and m can be an integer from 1 to 10.

The electron donor group, D and D', can typically create a ΔG<0 for formation of the anionic PTCDI radical. A variety of strong electron donor groups can be suitable. Suitable strong electron donor groups can be determined based on a variety of factors, such as oxidation and ionizing potential, nucleophilicity, steric hindrance and/or molecular geometry. Each of these factors can be used to identify strong reducing agents that are able to reduce the PTCDI core to an anionic radical. For example, D and D' can include at least one of:

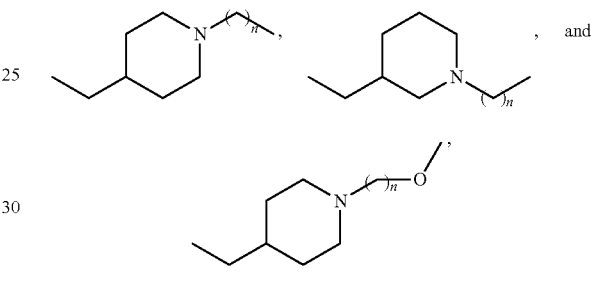

or the like, where n can typically range from 1 to 1000, from 1 to 50, or from 1 to 20. In yet other examples D and D' can include at least one of:

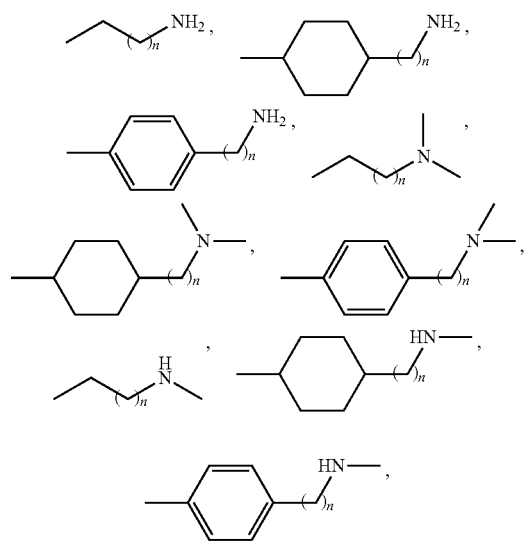

or the like, where n can range from 1 to 20, and in some cases 1 to 10. In some examples, the value for n can affect the length of the linker between the donor and PTCDI core. In such cases, n can generally range from 1 to 20, in some cases from 3 to 15, and in one example n can be 5. In yet other examples, D and D' can include at least one of:

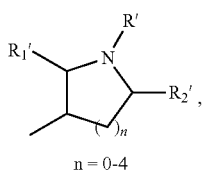 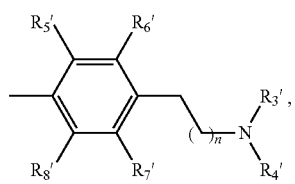

where n is 0-10,

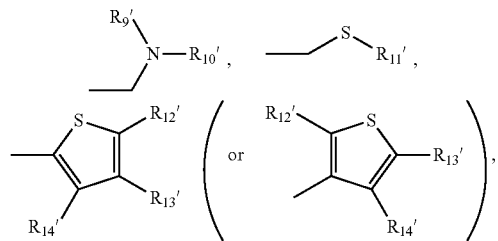

or the like, where $R_1'$—$R_{14}'$ can be substituted groups that do not eliminate the electron donating ability of D and D'. For example, $R_1'$—$R_{14}'$ can be independently selected from the group consisting of hydrogen, $C_1$-$C_5$ alkyl groups, $C_1$-$C_5$ alkyl ether groups, $C_6$-$C_9$ phenyl groups, and combinations thereof. In still other examples, D and D' can include at least one of:

or the like, where R"—$R_5$" can be substituted groups that do not eliminate the electron donating ability of D and D'. For example, R"—$R_5$" can be selected from the group consisting of hydrogen, $C_1$-$C_5$ alkyl groups, $C_1$-$C_5$ alkyl ether groups, $C_6$-$C_9$ phenyl groups, and combinations thereof. In one specific embodiment, at least one of -A-D and -A'-D' can be

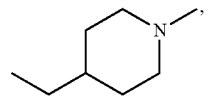

or the like, forming a 1-methylpiperdine-substituted perylene tetracarboxylic diimide (MP-PTCDI).

Thus, a variety of R groups, linking groups, and electron donor groups can be used to prepare the chemiresistive vapor sensor compounds. For example, non-limiting examples of chemiresistive vapor sensor compounds can include:

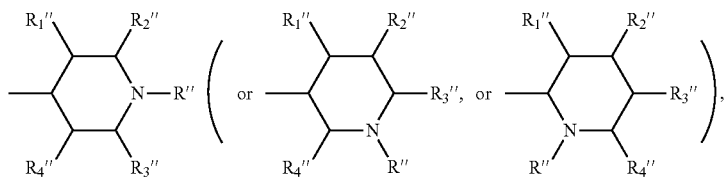

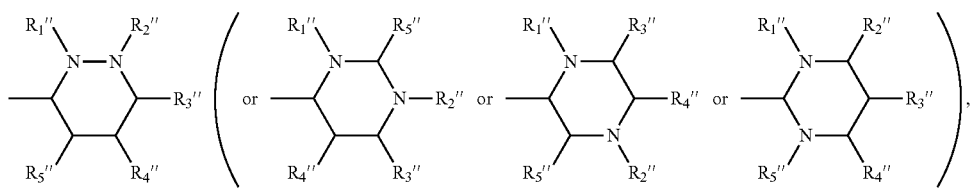

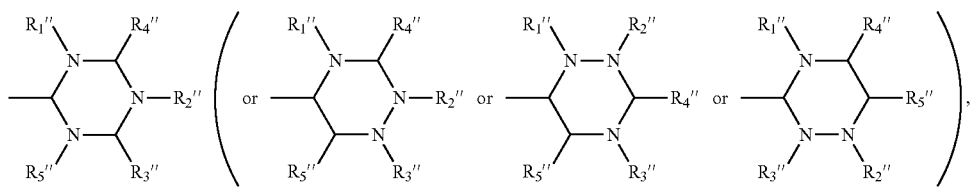

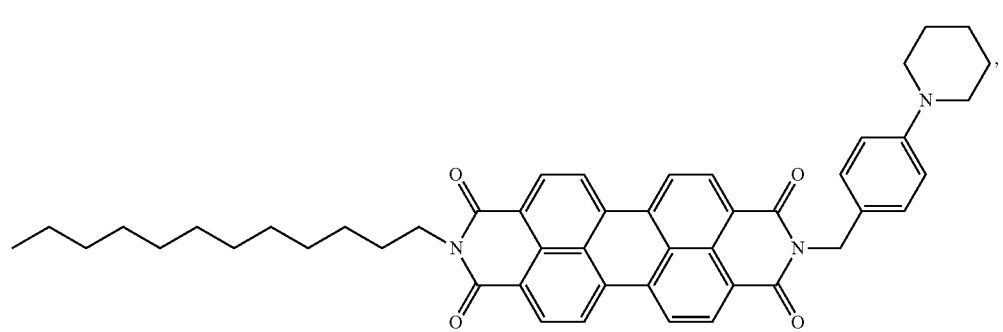
(IV)
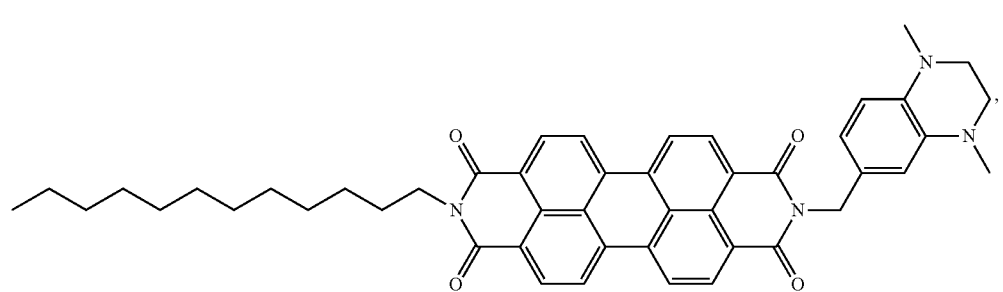
(V)
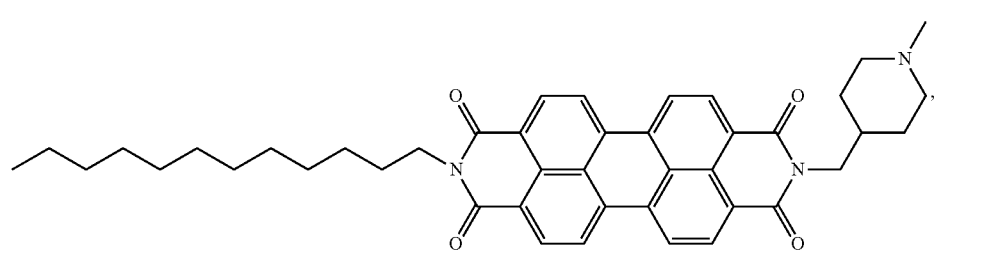
(VI)
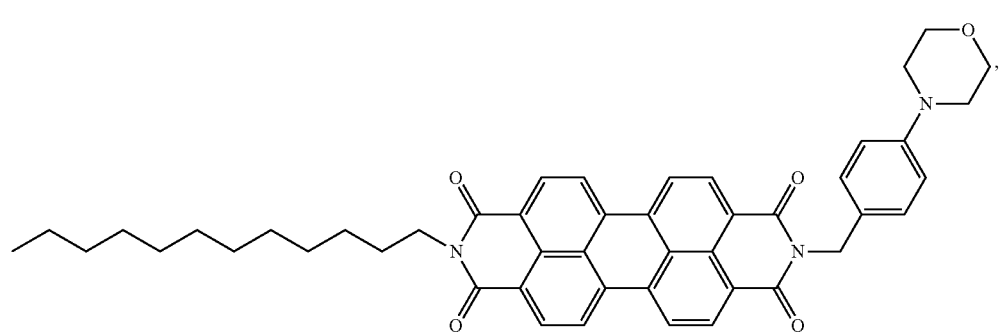
(VII)
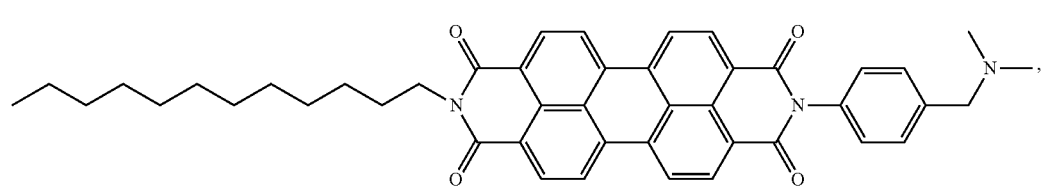
(VIII)
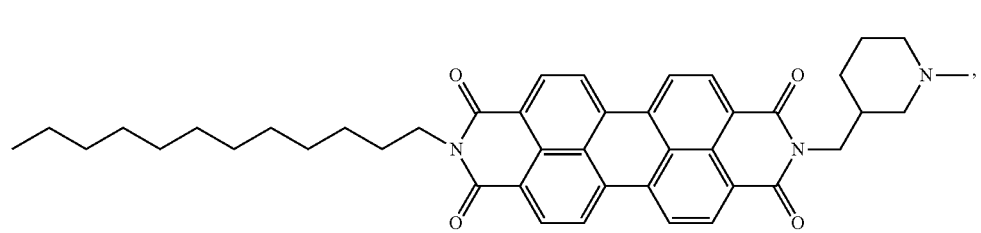
(IX)

-continued
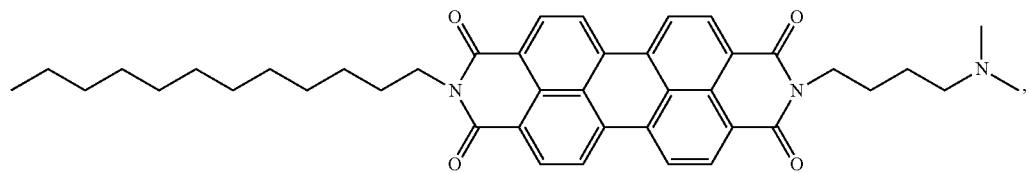
(X)
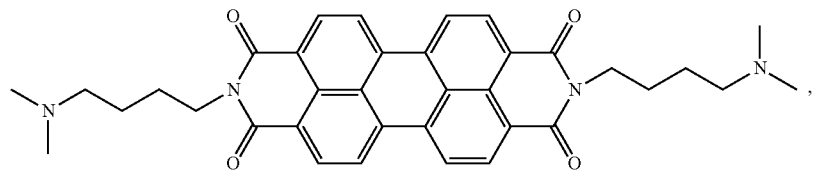
(XI)
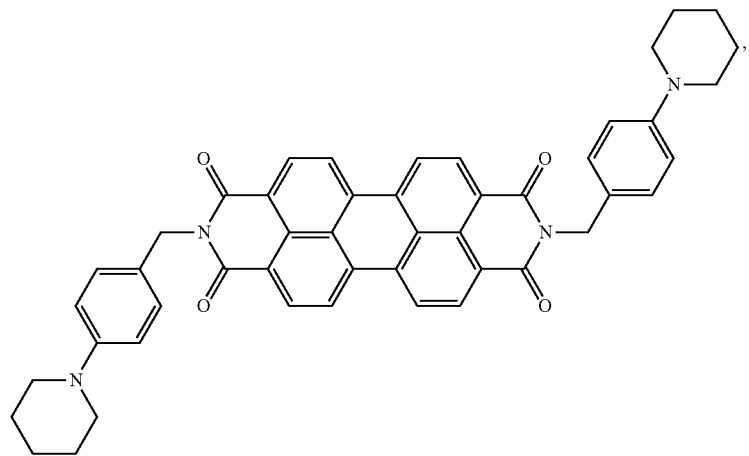
(XII)
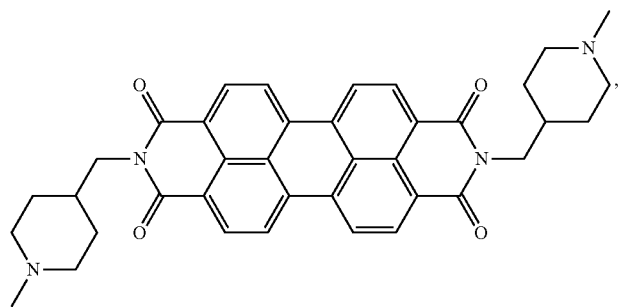
(XIII)
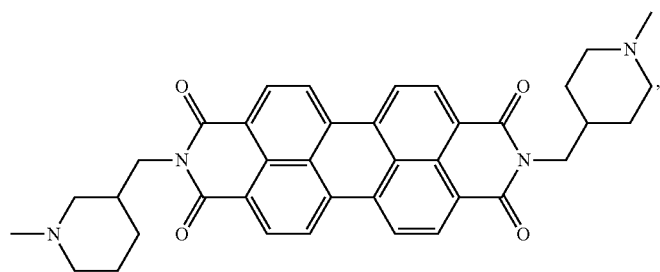
(XIV)

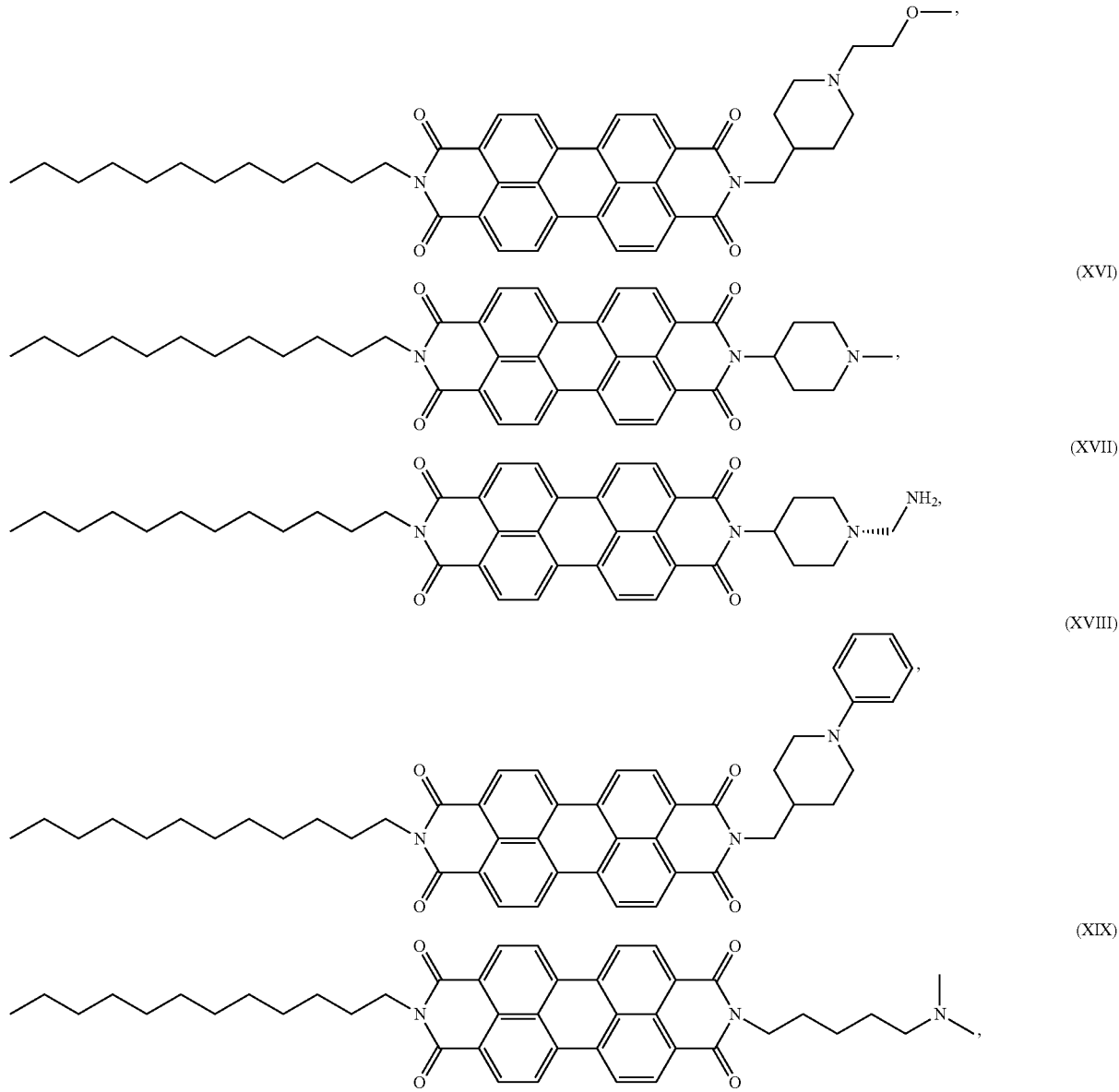

the like, or combinations thereof.

The individual chemiresistive vapor sensor compounds can form a variety of nanostructures depending on the different functional groups employed. In some examples, the nanostructures can form via co-facial stacking of individual chemiresistive vapor sensor compounds. Thus, the nanostructures can benefit from π-π interactions and bonding between adjacent compounds along the nanostructure. In some specific examples, the nanostructures can be formed via a self-assembly process. In one specific embodiment, the nanostructure can be a nanoribbon self-assembled through columnar π-π stacking and the PTCDI radicals can function as n-type dopants located in the lattice of PTCDI crystals along the nanoribbon.

The electron transfer of the nanostructure generally occurs from the electron donor portion of one sensor compound to the PTCDI portion of another adjacent sensor compound. This is generally illustrated in FIG. 1. As depicted in FIG. 1, a nanofiber 105 can include a plurality of chemiresistive vapor sensor compounds including a PTCDI core 110, an electron donor group 120, and a morphology control group 130 (or -A'-D' group). The electron donor group, such as electron donor group 120A, of one chemiresistive vapor sensor compound can donate an electron to the PTCDI core 110A of an adjacent chemiresistive vapor sensor compound. This can generate an anionic radical of the electron-accepting PTCDI core 110A without photo-excitation. As such, these materials can provide sensing of target compounds in the absence of photo-excitation. This affect is at least partially facilitated by the offset stacking of the compounds within the nanofiber. For example, without being bound to any one theory, it is thought that the inter-plane stacking is usually offset through longitudinal (along long axis of molecule) or lateral sliding, or rotation along the stacking direction, mainly determined by the maximal free energy change of the stacking (relative to the free molecules). Depending on the side groups, different PTCDIs possess different configuration of stacking that gives the maximal free energy change of stacking. Regardless, the electron donor and linking groups can be sufficient to form an anionic PTCDI radical of the PTCDI core by choosing donor groups with strong electron donation ability and nucleophilicity. The linking group length can also affect charge transfer. Typically, linking groups with a larger number of carbons can increase electron donation between the electron donor compound and an adjacent PTCDI core. As such, the linking group can typically have at least three carbons, although fewer carbons can be effective depending on the strength of the electron donor group.

Figure 2:
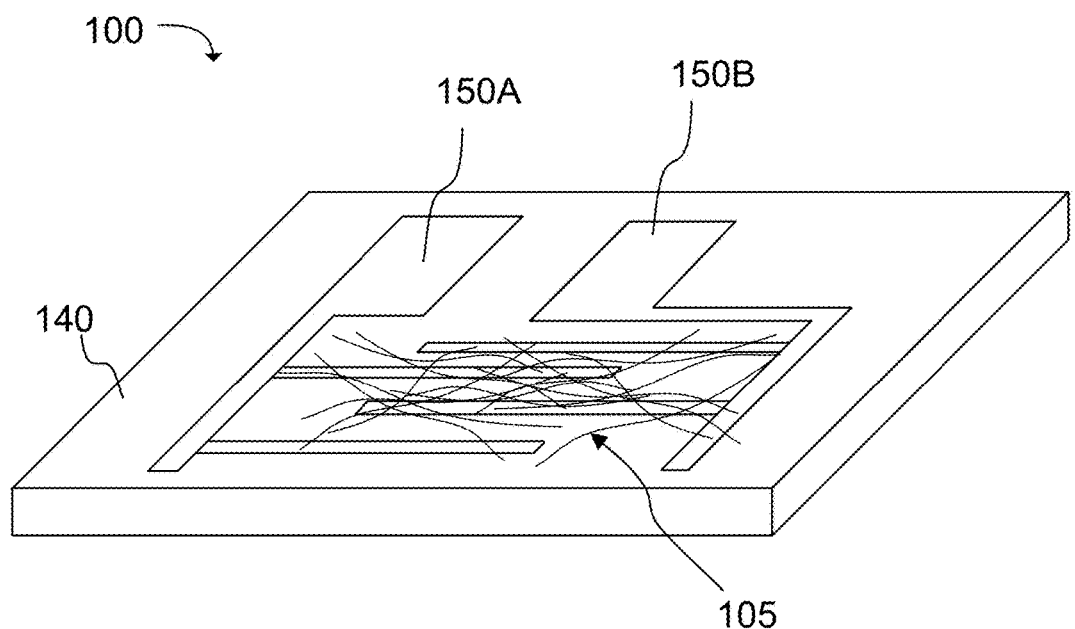
FIG. 2 is a schematic of nanofibers formed of chemiresistive vapor sensor compounds deposited on an interdigitated electrode (IDE), in accordance with some examples of the present disclosure.

The chemiresistive vapor sensor compounds and associated nanostructures described herein can be used to prepare a chemiresistive vapor sensor. For example, a chemiresistive vapor sensor for detection of a target compound can include an assembly of nanofibers formed of the chemiresistive sensor compound and a pair of electrodes operatively oriented about the assembly of nanofibers to allow electrical current to pass from a first electrode in the pair of electrodes through the assembly of nanofibers and to a second electrode in the pair of electrodes. This is generally illustrated in FIG. 2 with a pair of interdigitated electrodes. As depicted in FIG. 2, a chemiresistive vapor sensor 100 can include an assembly of nanofibers 105 formed of the chemiresistive vapor sensor compounds as described in more detail above. The assembly of nanofibers 105 can be deposited on a pair of electrodes including a first electrode 150A and a second electrode 150B, which can be formed on a substrate 140. In some examples, the pair of electrodes 150A and 150B can be interdigitated, although other electrode configurations can be used. The donor group of one sensor compound can donate electrons to an adjacent sensor compound along a nanofiber 105 to generate an electrical current. As such, the electrical current can pass from the first electrode 150A to the second electrode 150B via the nanofiber assembly. Thus, in some examples, when the sensor 100 is exposed to a target analyte, the target analyte can interact with the nanofiber assembly 105 via interfacial charge transfer, which can result in a detectable change in current across the electrode pair.

The target analyte or vapor can typically be an oxidizing vapor. Although the vapor can often comprise an oxidant, generally, the target vapor can include various explosives, toxic industrial compounds, chemical warfare compounds, and the like. Specific examples of the target oxidizing vapor can include, but is certainly not limited to, at least one of peroxides (e.g. triacetone triperoxide, hydrogen peroxide, etc), nitrogen oxides (e.g. nitromethane, dinitrotoluene, trinitrotoluene, ammonium nitrate fuel oil, ammonium nitrate, PETN, RDX, etc), toxic industrial compounds (e.g. chlorine, hydrogen peroxide, sulfur dioxide, hydrochloric acid, triethyl phosphate, phosphine, hydrogen cyanide, arsine, formaldehyde, etc), chemical warfare agents (e.g. triethylphosphate, dimethyl methylphosphonate, 2-chloroethyl ethyl sulfide, triphosgene, methyl salicylate, etc), and combinations thereof.

It is noted that the chemiresistive vapor sensor can include a variety of additional components or features. For example, the sensor can include a housing having an inlet and an outlet encompassing the pair of electrodes and an output electrically connected to the pair of electrodes to provide an indication of target compound detection. Additionally, in some examples, the sensor can have a forced air mechanism adapted to move air through the inlet and across the assembly of nanofibers. While photoexcitation is not necessary, the sensor can also include a light source for illuminating one or more detection zones (e.g. assembly of nanofibers). The addition of a light source can add cost and complexity, although such photoexcitation can sometimes further increase strength of detection signals.

The chemiresistive sensor can also be employed in a method of detecting target compounds. The method can include exposing the assembly of nanofibers to a suspected target compound source, measuring an electrical response of the assembly of nanofibers, and displaying a detection metric based on the electrical response. The detection metric can be one or more members selected from the group consisting of a change in electrical conductivity, change in electrical resistance, change in electrical current, and combinations thereof. The rate of change and/or recovery time varies with different analytes such that a correlation can be made using these changes and corresponding times for changes (e.g. a unique analyte response fingerprint). In one embodiment, the sensor can have a detection limit down to 100 ppb or lower, down to 200 ppb or lower, or down to 600 ppb or lower. Further, in some examples, the detector response time can be from about 5 seconds to about 120 seconds, about 10 to about 100 seconds, or about 5 seconds to about 30 seconds or 60 seconds. In many cases, the assembly of nanofibers can be responsive in the absence of exposure to light. However, in some cases, the assembly of nanofibers can be additionally exposed to light sufficient to produce distinguishable or augmented current changes upon exposure to a target compound. Depending on the target compound, the change in current can be either positive or negative.

EXAMPLES

Figure 3:
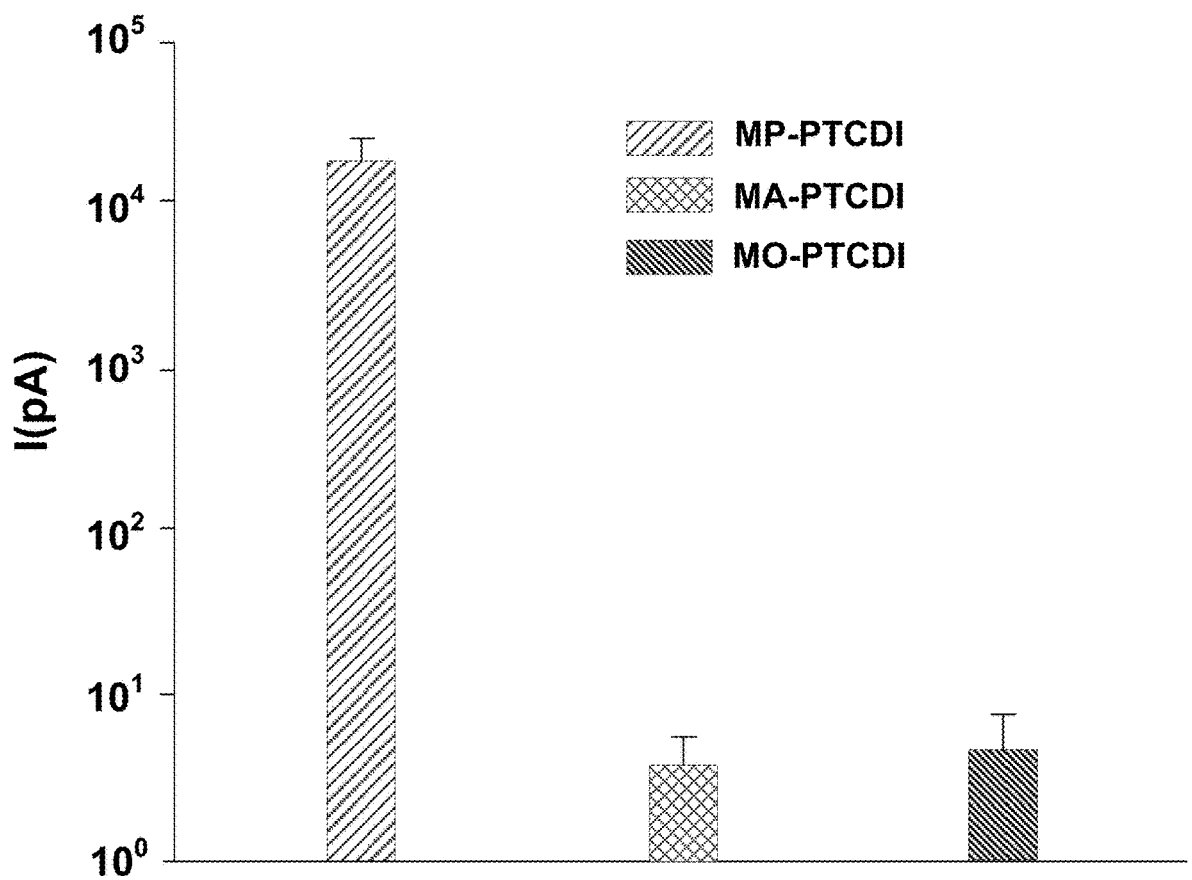
FIG. 3 is a comparison of electrical current measured through three PTCDI nanoribbons. The current values were measured at a bias of 10 V.

Chemical Self-Doping of One-Dimensional Organic Nanomaterials for High Conductivity Application in Chemiresistive Sensing Target Gas or Vapor PTCDI molecules were substituted with 1-methylpiperidine (MP) to construct self-doped semiconductor through one-dimensional (1D) self-assembly of the molecules into nanoribbon structures. The methylpiperidine moiety on one molecule, acting as a strong electron donor (D), interacted with a PTCDI core on an adjacent molecule (acting as the electron acceptor, A), generating anionic radicals of PTCDI. The resultant radicals functioned as the n-type dopants located in the lattice of PTCDI semiconductors. A similar side-group induced self-doping can also be exploited in other conducting polymer materials, e.g., polyaniline. The nanoribbon structure, dominated by the π-π stacking between the PTCDI planes, provides an efficient pathway for long-range charge transport. As a result, the self-doped electrons migrated along the long axis of the nanoribbon structure, leading to enhanced conductivity. The nanoribbons can exhibit four orders of magnitude higher current as compared to 1D nanomaterials assembled from other PTCDI molecules under the same test conditions (See FIG. 3).

With high conductivity, the n-type PTCDI nanoribbons can be used in a chemiresistive sensor for detection of electron deficient chemicals with a high signal-to-noise ratio, providing a reliable output signal and low limit of detection. The PTCDI nanoribbons demonstrate a sensitive chemiresistive response to hydrogen peroxide ($H_2O_2$) vapor, allowing application of the chemiresistive sensor in detection of improvised explosives, such as triacetone triperoxide (TATP), diacetone diperoxide (DADP), hexamethylene triperoxide diamine (HMTD), and simple liquid mixtures of concentrated hydrogen peroxide and fuels (e.g., alcohols, acetone). $H_2O_2$ is commonly used as the chemical marker of these peroxide explosives. Current techniques for detecting $H_2O_2$ are fluorometric, colorimetric, and electrochemical methods, but most of them are limited to detection in the liquid phase. It is still challenging to detect $H_2O_2$ vapor at trace levels. Thus, the chemiresistive sensing technique described herein has the advantages in trace vapor detection and facilitates the fabrication of a portable, low-power, and simple sensor device.

Synthesis of Core Compound and Fabrication of Nanostructures

The precursor compound, N-dodecyl-perylene-3,4,9,10-tetracarboxylic monoimide monoanhydride, was synthesized. Subsequently, the precursor compound (100 mg), (1-methyl-4-piperidinyl)methanamine (Sigma-Aldrich, 71.3 mg), zinc acetate (Sigma-Aldrich, ACS reagent, 98%, 3.0 mg) and imidazole (Sigma-Aldrich, ACS reagent, >99%, 1.5 g) were combined and heated to 150° C. for 8 hours. After cooling to room temperature, the reaction mixture was dispersed in 10% HCl (Fisher Chemical, 36.5 to 38.0%, w/w) solution to solubilize the imidazole, the insoluble product was collected by filtration and washed with water and methanol. The crude product was converted to the free base by dissolving in chloroform and washing with 10% NaOH (Sigma-Aldrich, ACS reagent, >97.0%) solution. The organic layer was washed with water and dried over anhydrous $Na_2SO_4$ (Sigma-Aldrich, ACS reagent, >99%). The reaction mixture was then purified by silica gel chromatography using 6.0% ethanol in chloroform as the eluent followed by recrystallization from chloroform/ethanol to give final product (54.7 mg, 46%).

Self-assembly of the MP-PTCDI molecules was performed through a solvent exchange process from a "good" solvent to a "bad" solvent, where the molecules have limited solubility in the "bad" solvent and thus self-assemble into one-dimensional nanostructures via molecular stacking. A solution injection method was used to conduct the self-assembly in ethanol. Typically, 0.4 mL of MP-PTCDI solution (1.5 mmol/L) in chloroform was injected rapidly into a larger volume of ethanol (4 mL) and placed in the dark for 5 hours. The nanoribbons were then transferred to substrates for further characterization and electrical measurements. Synthesis of MA-PTCDI (PTCDI with a dimethylaniline moiety) and MO-PTCDI (PTCDI with a methoxyphenyl moiety), and self-assembly into nanoribbons were performed according to similar methods.

PTCDI-based molecules have been extensively explored for 1D self-assembly and optoelectronic applications in recent years. PTCDI molecules have nodes in the π-orbitals, which allows side-chain substitutions to play an important role in intermolecular interactions, resulting in different electronic properties through charge transfer.

Figure 4:
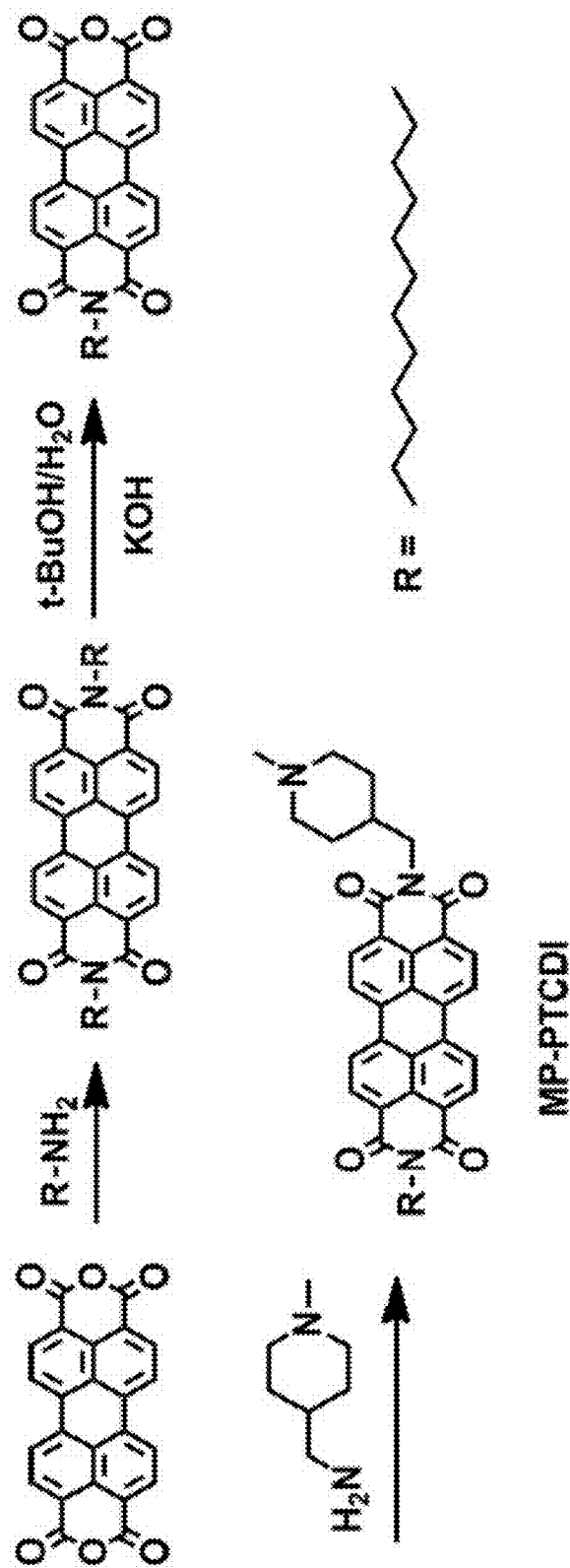
FIG. 4 depicts a synthetic route for 1-methylpiperdine-substituted perylene tetracarboxylic diimide (MP-PTCDI), in accordance with some examples of the present disclosure.
Figure 5A:
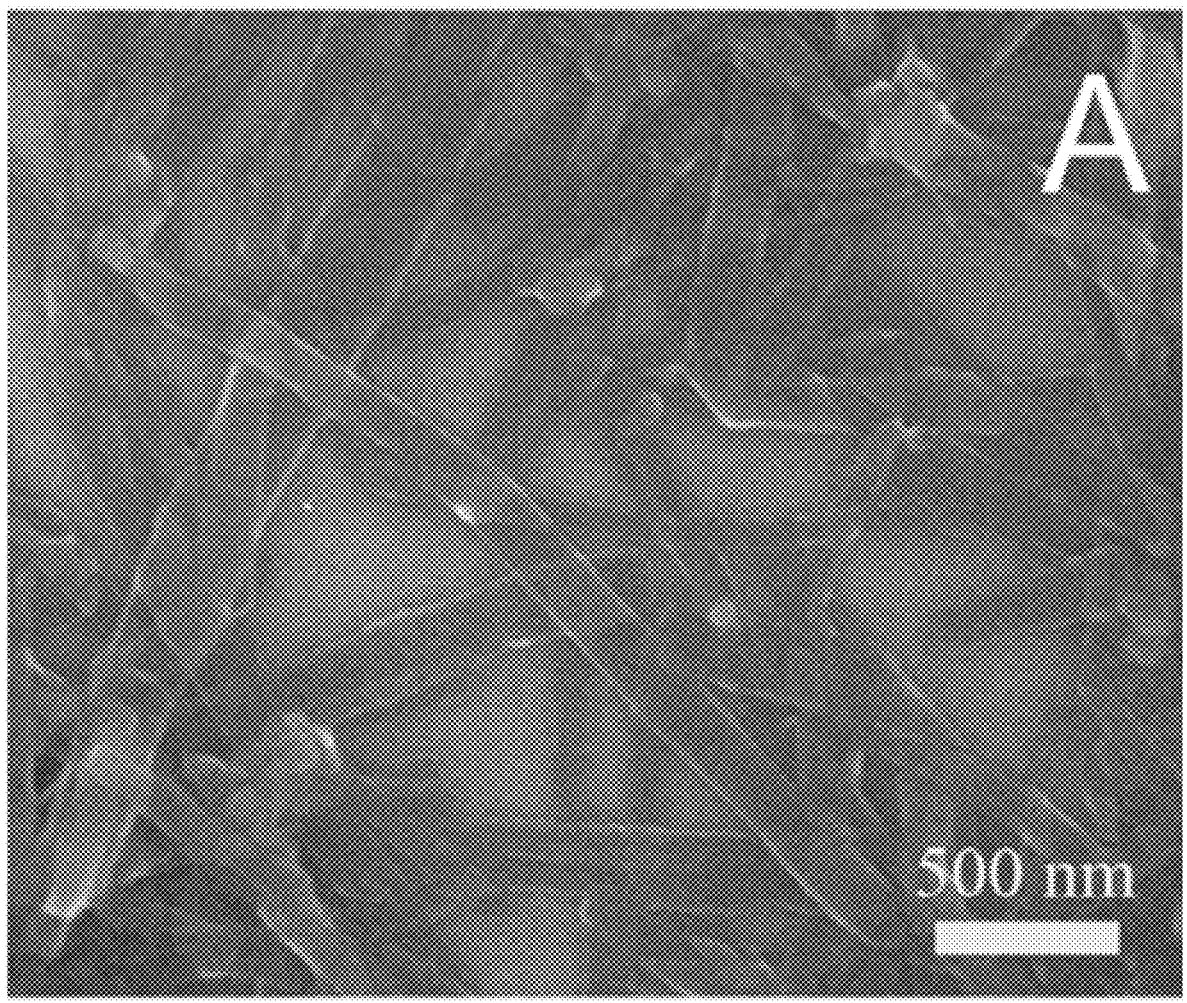
FIG. 5A is a SEM image of MP-PTCDI nanoribbons.
Figure 5C:
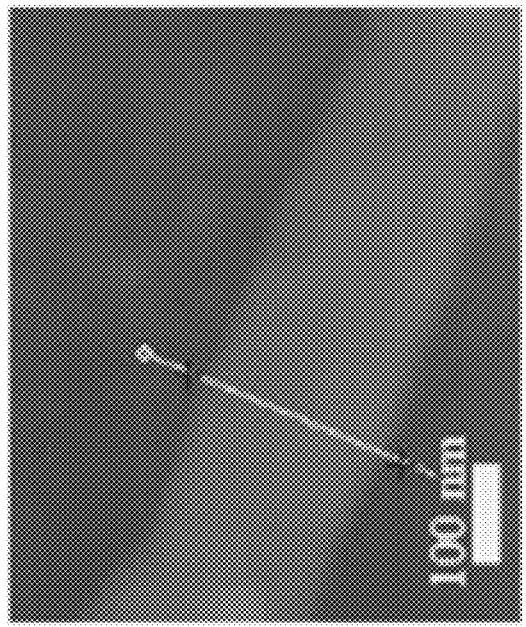
FIG. 5C is a close-up view of a selected area of the AFM image illustrated in FIG. 5B.
Figure 5B:
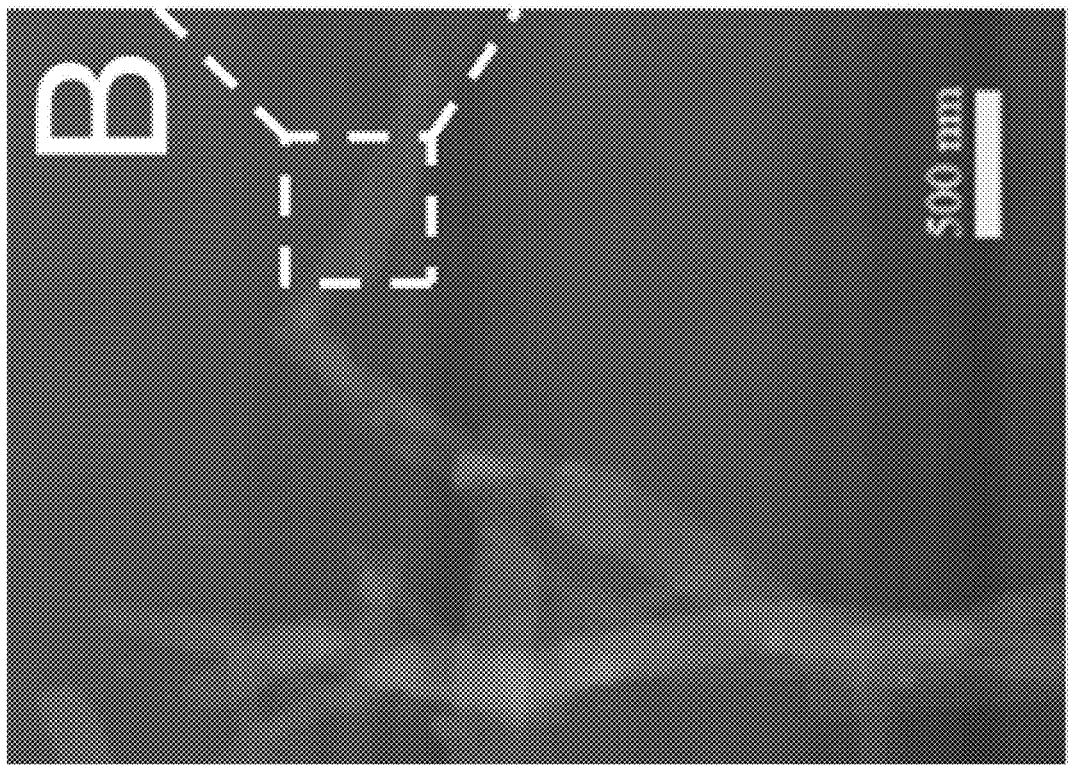
FIG. 5B is an AFM image of MP-PTCDI nanoribbons.
Figure 5D:
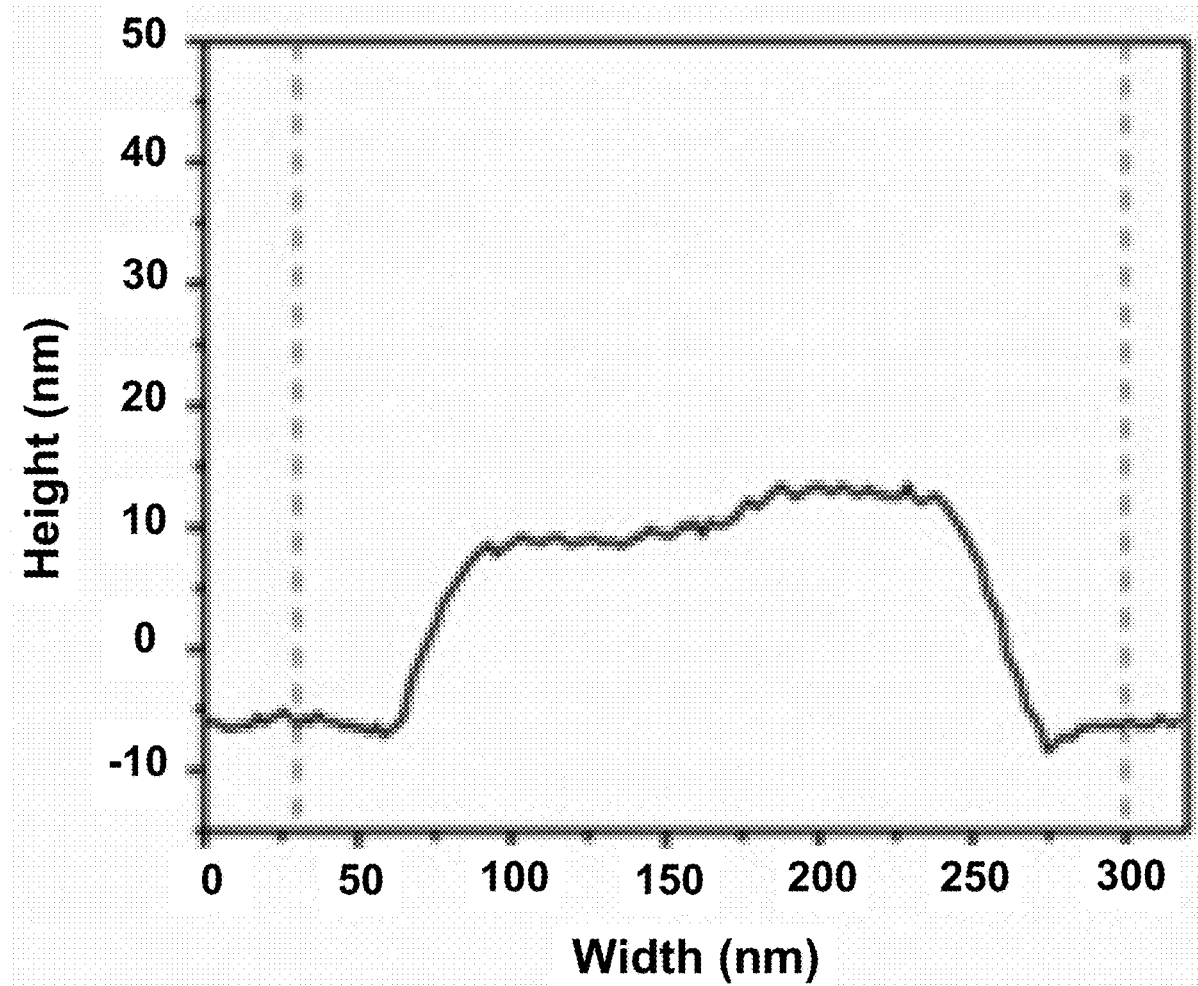
FIG. 5D is a line-scan profile of a single MP-PTCDI nanoribbon at a selected position.

For example, a PTCDI molecule substituted with a 1-methylpiperidine moiety was designed and synthesized as described above and as illustrated in FIG. 4. The MP-PTCDI nanoribbons were fabricated using the previously reported solution phase self-assembly method. The morphology of MP-PTCDI nanoribbons was characterized by SEM and AFM (FIGS. 5A-5D). The nanoribbons are several micrometers in length and 100-300 nm in width. The thickness of the nanoribbons is estimated to be just about 15 nm (FIGS. 5B-5D, AFM image and line-scan profile). Such shape-defined 1D nanostructures are conducive to the construction of electronic devices. For comparative study, two other PTCDI molecules, MA-PTCDI and MO-PTCDI (both substituted with the same dodecyl alkyl chain, but with different groups on the other end, were also synthesized and assembled into nanoribbon structures. Owing to the similar molecular structure, the two reference PTCDIs formed about the same nanoribbon morphology as the MP-PTCDI. The dimethylaniline moiety of MA-PTCDI acts as a strong electron donor (under photoexcitation), whereas the methoxyphenyl is a less effective donor to PTCDI.

Characterization and Measurements

For materials characterization, UV-Vis absorption spectra were collected with an Agilent Cary 100. Fluorescence spectra were acquired on an Agilent Eclipse spectrophotometer. The bright field and fluorescence optical images were obtained with a Leica DMI4000B inverted microscope equipped with an Acton SP-2356 Imaging Spectrograph system and Princeton Instrument Acton PIXIS: 400B Digital CCD Camera System for high resolution imaging. AFM measurements were carried out on a Veeco MultiMode V scanning probe microscope in tapping mode. SEM measurement was performed with an FEI Nova Nano 630 (FEI Corporation) with a helix detector in low vacuum (0.43 Torr water pressure). To make samples for either AFM or SEM measurements, the MP-PTCDI nanoribbons were directly transferred from ethanol and deposited onto a silicon substrate coated with a polished 300 nm thick $SiO_2$ layer, and then dried in vacuum oven at room temperature in the dark.

For current measurement, interdigitated electrodes (IDE) were used for all current measurements. The IDE has a channel width of 2100 μm and a gap length of 50 μm, and was fabricated by a standard photolithography procedure on a silicon wafer with a 300 nm thermal oxide layer (Silicon Quest International). The electrodes were made by sputtering with 20 nm titanium adhesion layer and 50 nm gold layer. MP-PTCDI nanoribbons were deposited onto IDE by drop-casting, followed by drying in vacuum oven at room temperature in the dark. The electrical conductivity was measured under ambient conditions using a two-probe method on a Signatone S-1160 Probe Station combined with an Agilent 4156C Precision Semiconductor Analyzer. To compare the conductivity of different PTCDI nanomaterials, 12 nmol PTCDI nanomaterials were deposited onto the IDE by drop-casting and the conductivity was tested under the same conditions. To compare the current enhancement ratio after surface coating with amines, 12 nmol of CH-PTCDI nanobelts were chosen as the standard, zero-doping material, and deposited onto the IDE. 1 μL of methanol solution containing different concentrations of the amines (1-methylpiperidine, TCI America, >99.0%; hexylamine, Acros Organics, 99%; triethylamine, Sigma-Aldrich, 99%; aniline, Acros Organics, 99.5%, extra pure) were drop cast onto the surface of the CH-PTCDI nanobelts, providing the varying molar amount of amine coated on the surface. To avoid the oxidation of amines during processing, the fresh amine solution was made for each measurement. $^1$H NMR measurements were conducted for all the amines during the project period to assure that the high purity of amines remained throughout the experiments.

Nanoribbon Conductivity

MP-PTCDI nanoribbons possess a high electrical conductivity. For example, the current of the MP-PTCDI nanoribbons is four orders of magnitude higher than MA- and MO-PTCDI nanoribbon materials under the same test conditions. Considering the similar nanoribbon structures formed from other PTCDIs and the fact that the π-electronic property of PTCDI backbone remains unchanged with different side-substitutions, it is suspected that the high conductivity observed for MP-PTCDI nanoribbons is largely caused by the methylpiperidine moiety.

Figure 6A:
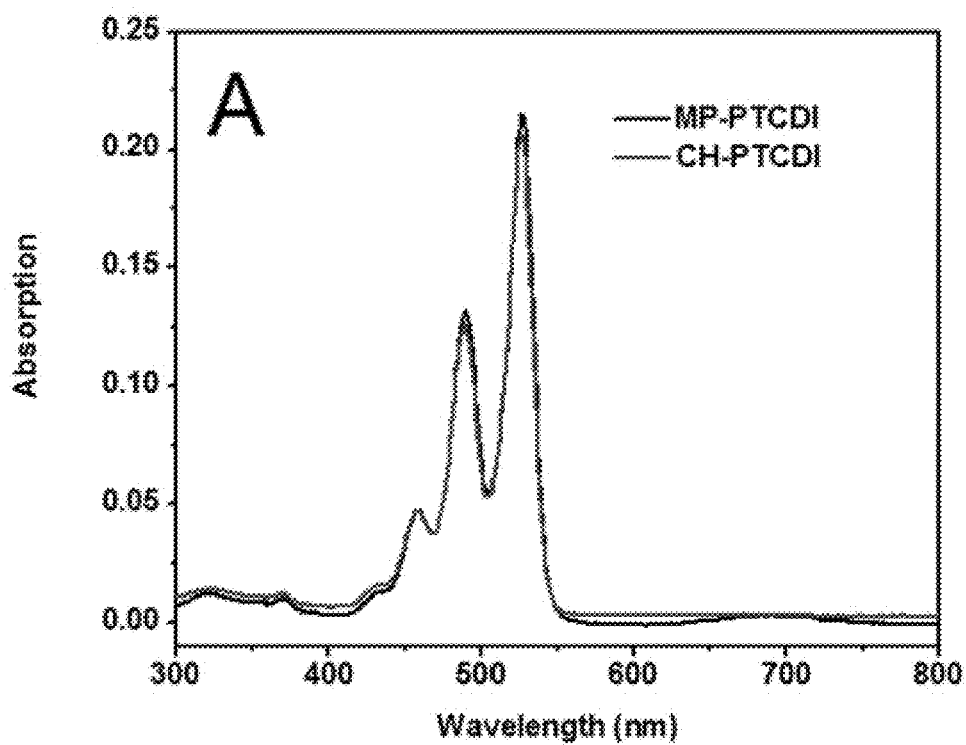
FIG. 6A is UV-Vis absorption spectra of a chloroform solution (10 µmol $L^{-1}$) of MP-PTCDI and CH-PTCDI.
Figure 6B:
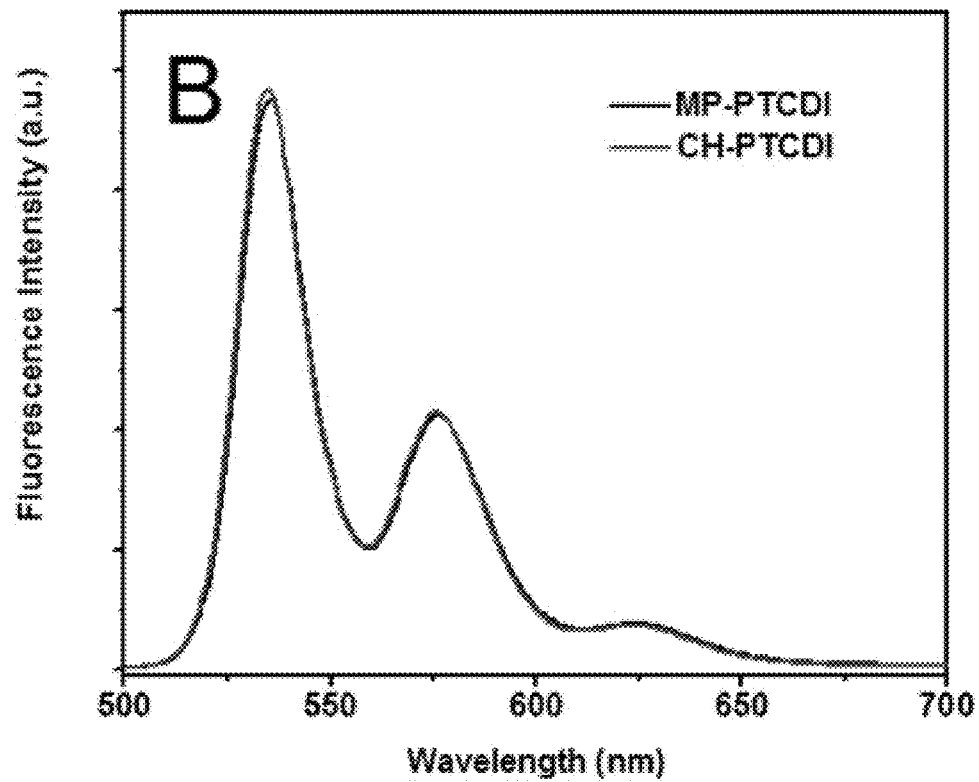
FIG. 6B is fluorescence spectra of the chloroform solution (10 µmol $L^{-1}$) of MP-PTCDI and CH-PTCDI.
Figure 6C:
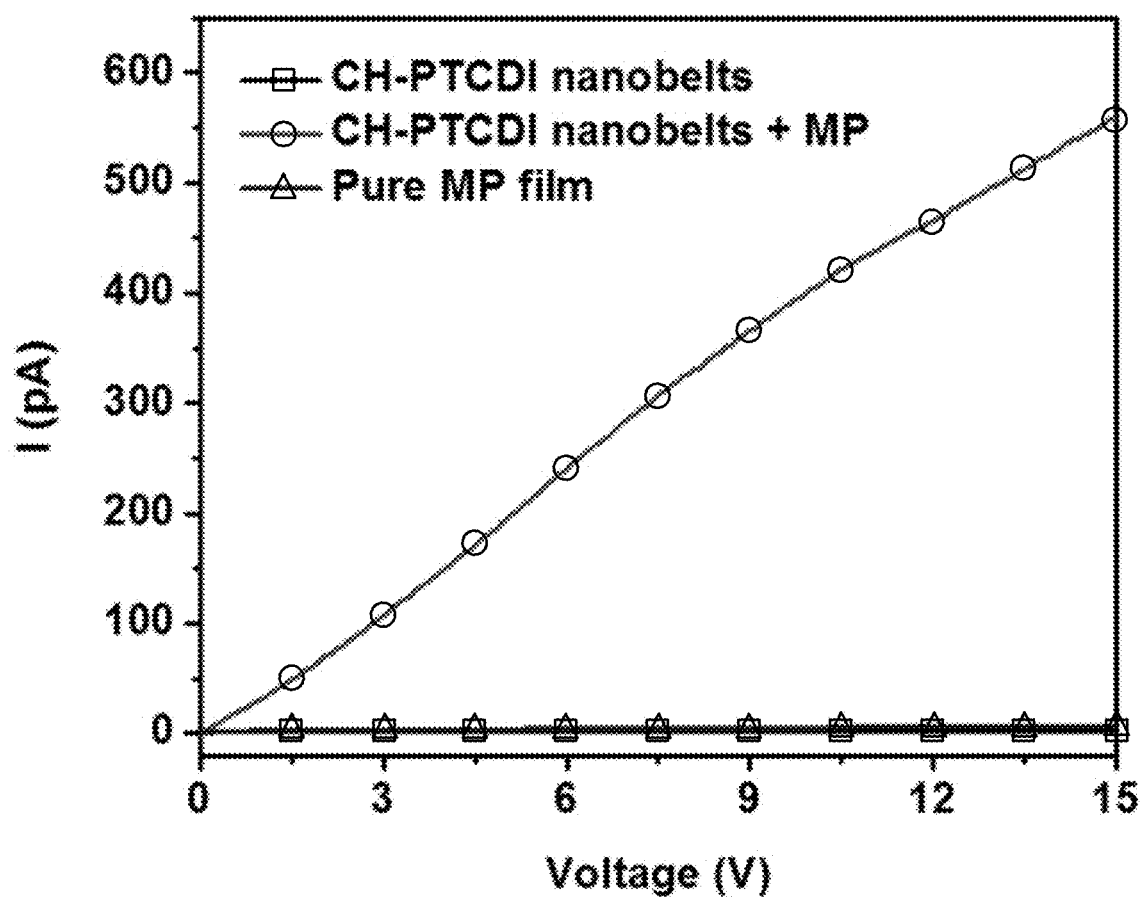
FIG. 6C is a graphical display of I-V curves of the CH-PTCDI nanobelts before and after surface coating with 2 µmol 1-methylpieridine (MP). The pure 1-methyliperidine thin film drop-cast of 4 µmol is slightly conductive.
Figure 13A:
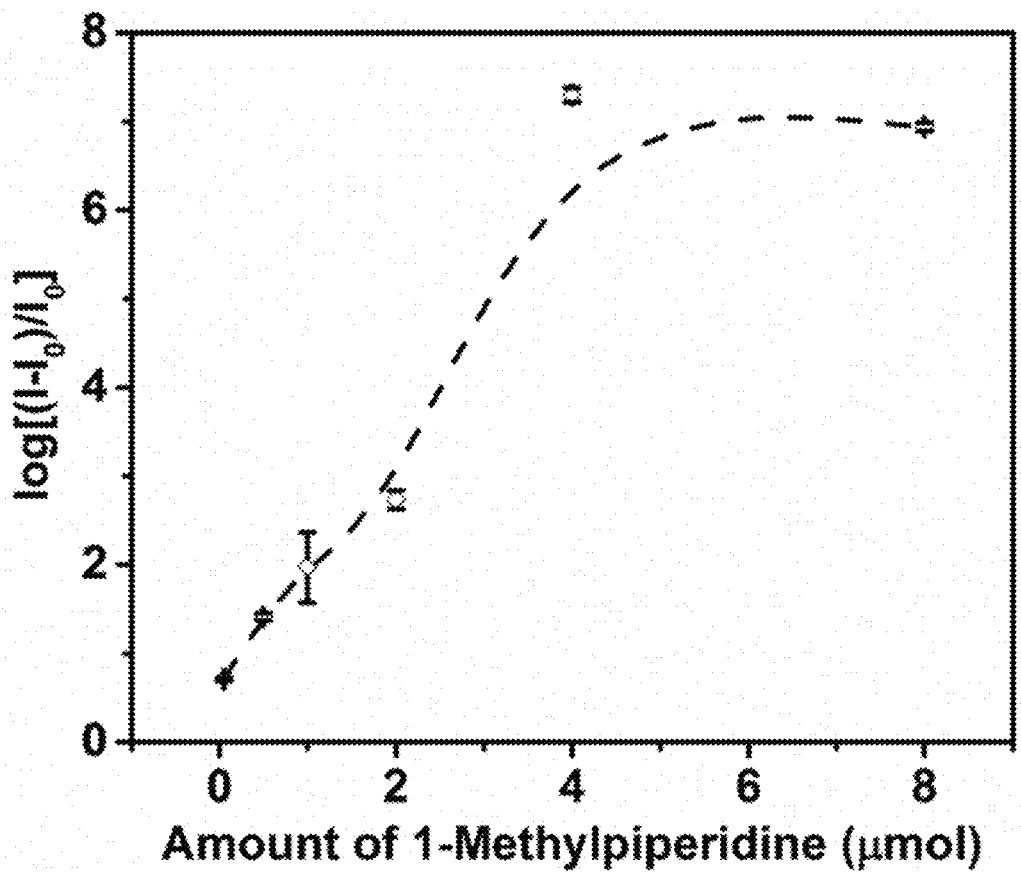
FIG. 13A depicts the current enhancement ratio, $(I-I_0)/I_0$, measured over the CH-PTCDI nanobelts when coated with varying molar amounts of 1-methylpiperidine, where $I_0$ is the current of pristine CH-PTCDI nanobelts, and I is the current measured on the same nanobelts after coated with 1-methylpiperidine. All the current values were obtained at a bias of 10 V.

To gain insight into the high conductivity of MP-PTCDI nanoribbons, a case study model was constructed by coating 1-methylpiperidine molecules on N,N'-di(cyclohexyl)-perylene-3,4,9,10-tetracarboxylic diimide (CH-PTCDI) nanobelts to investigate the influence of this specific substitution group on the conductivity of one-dimensional PTCDI nanomaterials. The CH-PTCDI was selected because the cyclohexyl side-chain groups are neutral and inactive in charge transfer interactions, and the shape defined nanobelts can be easily fabricated from this molecule with high reproducibility. In this study, 12 nmol of CH-PTCDI nanobelts were deposited onto interdigitated electrodes (IDEs) patterned on a silicon wafer, and a controlled amount of 1-methylpiperidine was drop-cast onto the nanobelts. Negligible currents were measured for either pristine CH-PTCDI nanobelts (0.0012 nA at a bias of 10 V, FIG. 6C) or pure 1-methylpiperidine film drop-cast from 4 µmol amount (0.0055 nA at a bias of 10 V, FIG. 6C). In contrast, a much increased current was observed for the CH-PTCDI nanobelts coated with only 2 µmol of 1-methylpiperidine (0.45 nA at a bias of 10 V, FIG. 6C). The current increased further when more 1-methylpiperidine was deposited. The current increased to 32.5 µA, an enhancement ratio of $2 \times 10^7$ compared to the pristine nanobelt, when 4 µmol of 1-methylpiperidine was deposited (FIG. 13A). An enhancement ratio of $8 \times 10^6$ was observed when 8 µmol of 1-methylpiperidine was deposited, indicating that the current increase started to reach saturation when more than 4 µmol of 1-methylpiperidine was cast (FIG. 13A). This significant increase in conductivity is likely due to the chemical doping, which occurs through the donor-acceptor (charge transfer) interaction between 1-methylpiperidine and PTCDI.

Figure 7A:
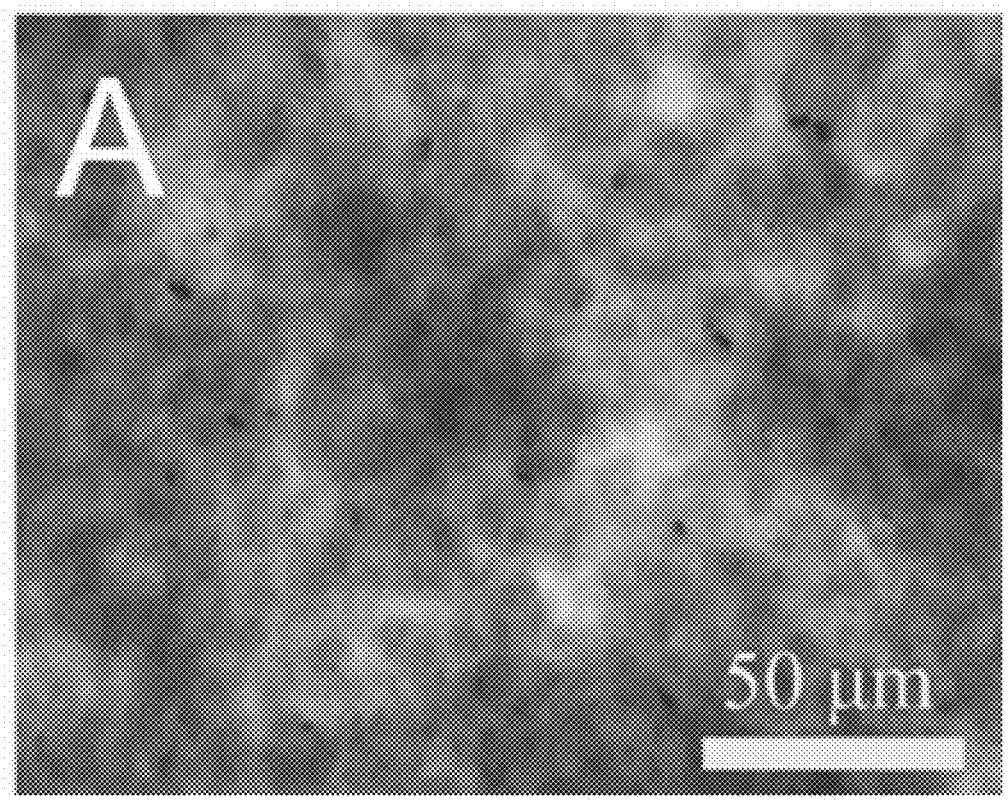
FIG. 7A is a bright-field microscopy image of MP-PTCDI nanoribbons deposited on a quartz slide.
Figure 7B:
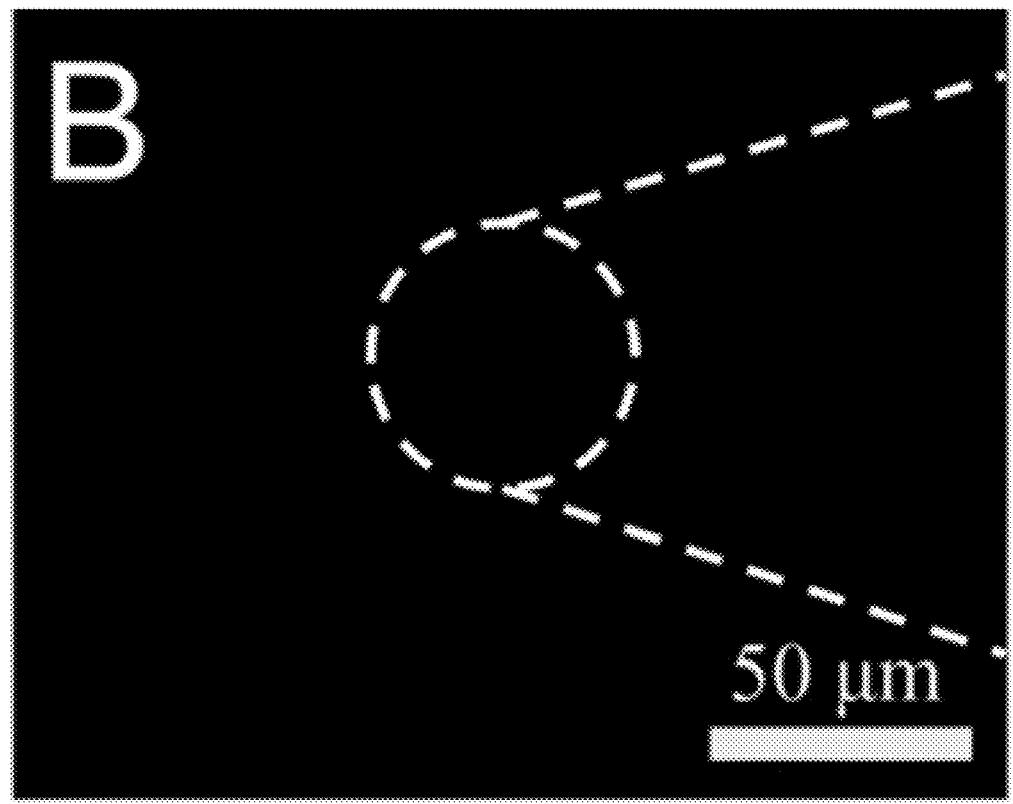
FIG. 7B is a fluorescent optical microscopy image of MP-PTCDI nanoribbons deposited on a quartz slide.
Figure 7C:
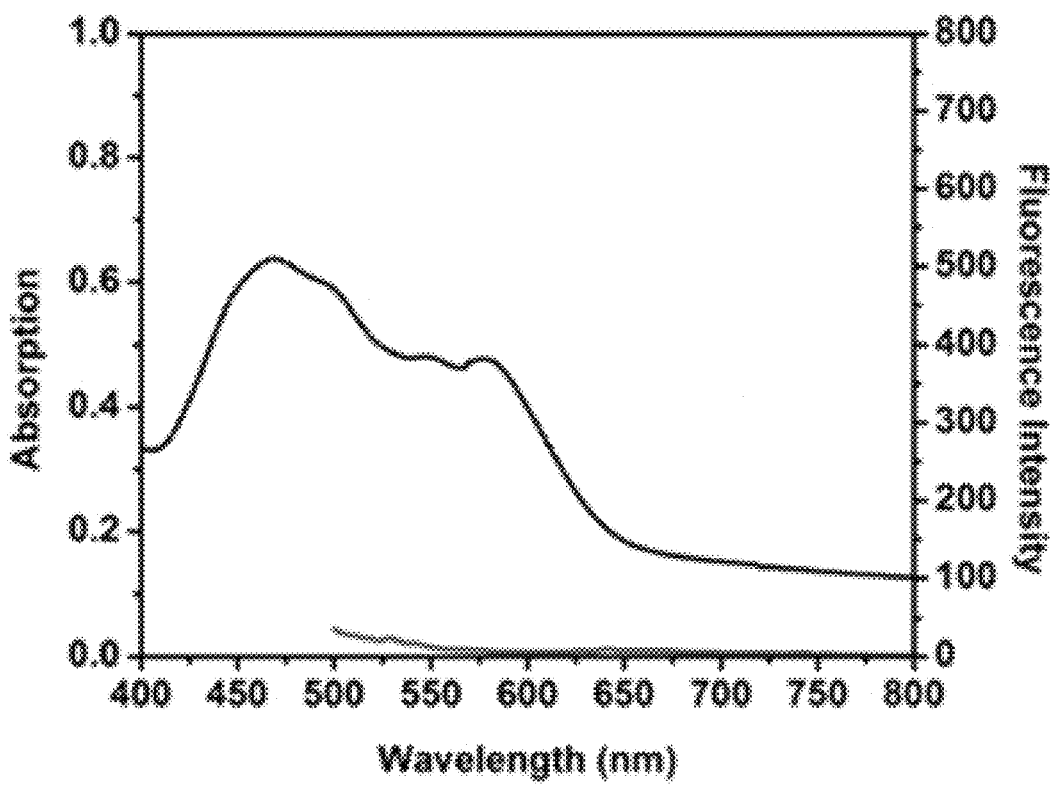
FIG. 7C is UV-Vis absorption and fluorescence spectra of MP-PTCDI nanoribbons in selected area (white cycle) of FIG. 7B.
Figure 7D:
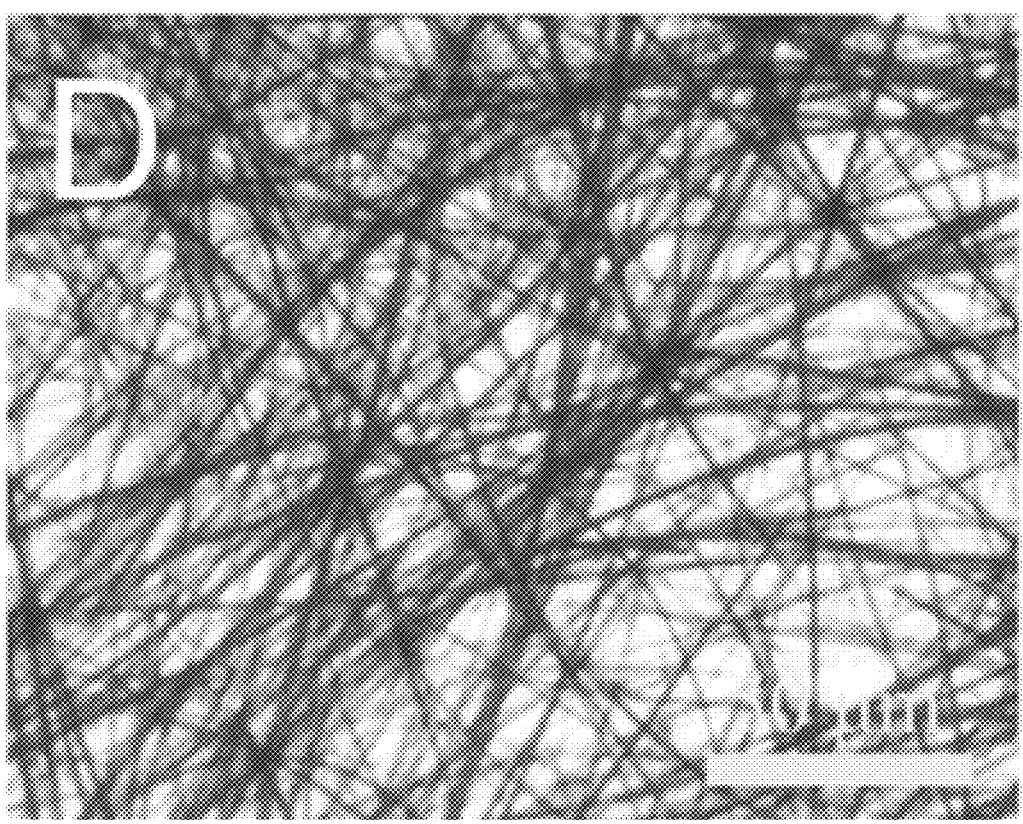
FIG. 7D is a bright-field microscopy image of CH-PTCDI nanobelts deposited on quartz slide.
Figure 7E:
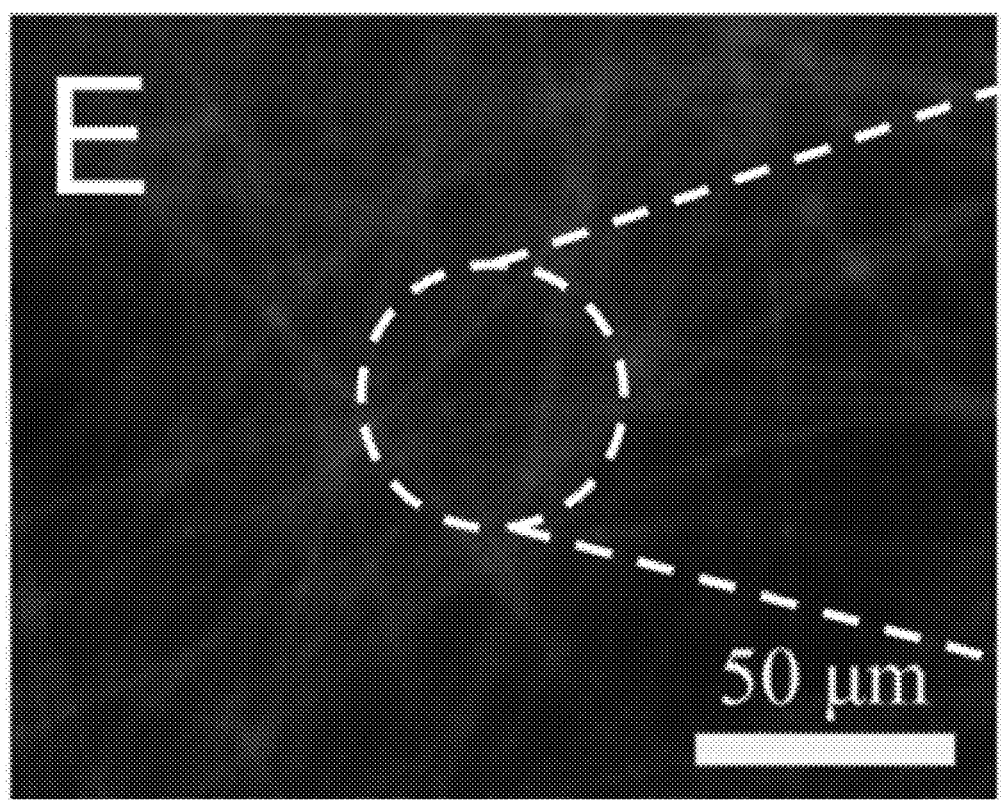
FIG. 7E is a fluorescent optical microscopy image of CH-PTCDI nanobelts deposited on quartz slide.
Figure 7F:
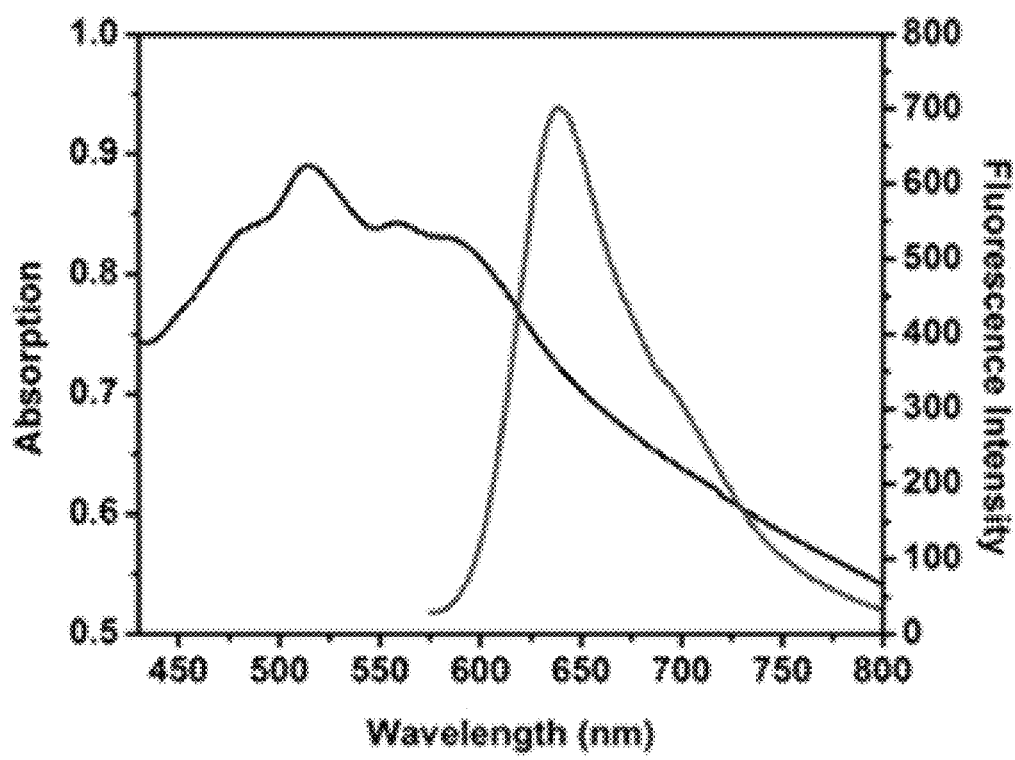
FIG. 7F is UV-Vis absorption and fluorescence spectra of CH-PTCDI nanobelts in selected area (white cycle) of FIG. 7E.
Figure 8A:
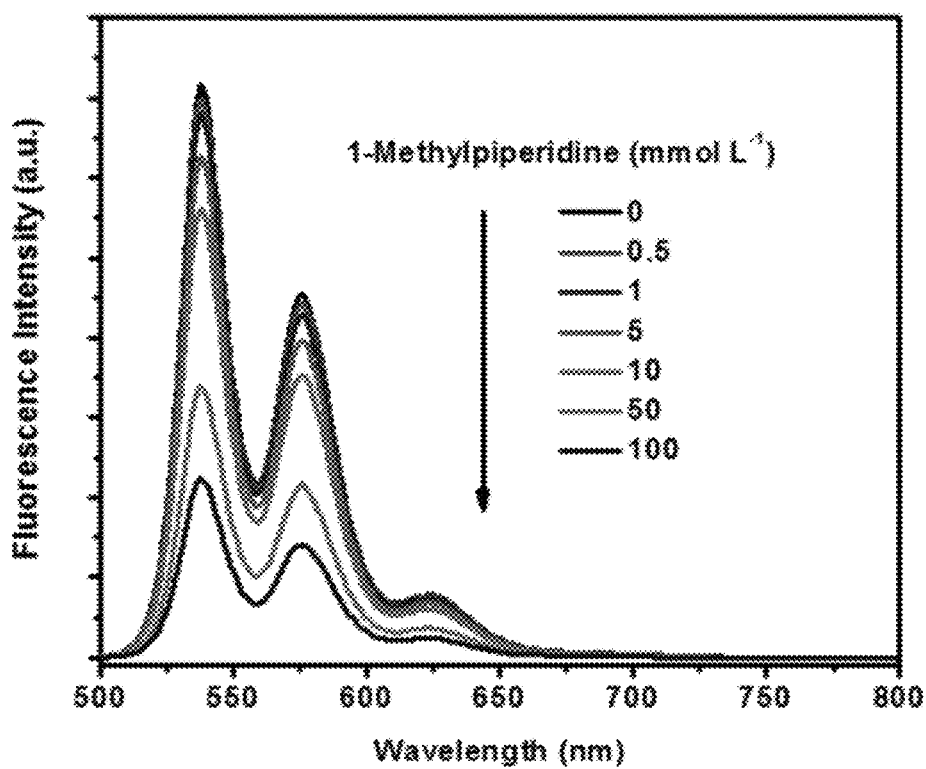
FIG. 8A is fluorescence spectra of CH-PTCDI solution in chloroform (10 µmol $L^{-1}$) upon addition of 1-methylpiperidine at varying concentrations.
Figure 8B:
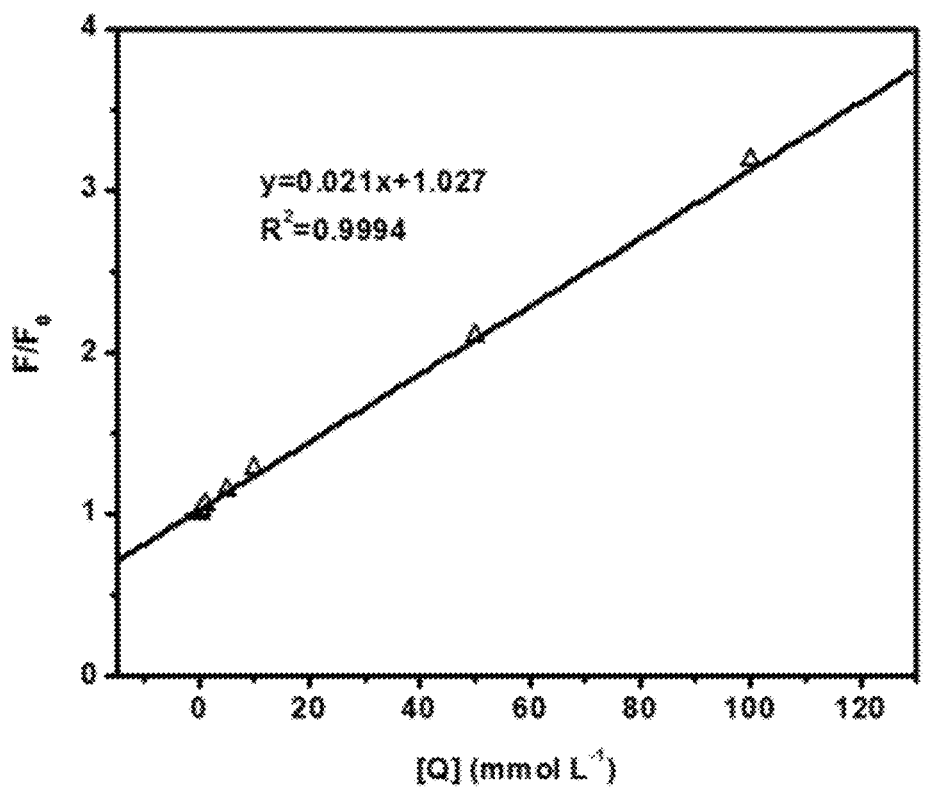
FIG. 8B is a Stern-Volmer plot of the fluorescence quenching shown in FIG. 8A.

The charge transfer interaction between 1-methylpiperidine and CH-PTCDI was also confirmed by the fluorescence quenching measurements of PTCDI. MP-PTCDI solution in chloroform exhibits strong fluorescence emission, comparable to CH-PTCDI molecules in chloroform (FIGS. 6A-6B), indicating that there is no intramolecular electron transfer in the MP-PTCDI molecule. However, no fluorescence emission was observed for the nanoribbons fabricated from the MP-PTCDI molecules (FIGS. 7A-C). By contrast, the CH-PTCDI nanobelts still have considerable fluorescence emission (FIGS. 7D-F). The fluorescence quenching within MP-PTCDI nanoribbons is likely caused by the intermolecular electron transfer between 1-methylpiperidine on one molecule and the PTCDI part on the other molecule. To prove this intermolecular charge transfer, fluorescence spectra of the reference PTCDI, CH-PTCDI, were measured in chloroform solutions with and without addition of 1-methylpiperidine (FIG. 8A). Significant fluorescence quenching (indicative of charge transfer interaction) was observed with increasing concentrations of 1-methylpiperidine, which follows the linear Stern-Volmer relationship (FIG. 8B). The linear fitting gives the binding constant of 21.6 $M^{-1}$ between 1-methylpiperidine and the PTCDI. The binding constant obtained is about one order of magnitude higher than those measured for the aromatic hydrocarbon donor-acceptor complexes. The enhanced binding is largely due to the stronger electron donating capability of organic amines, compared to the aromatic hydrocarbons.

Figure 9A:
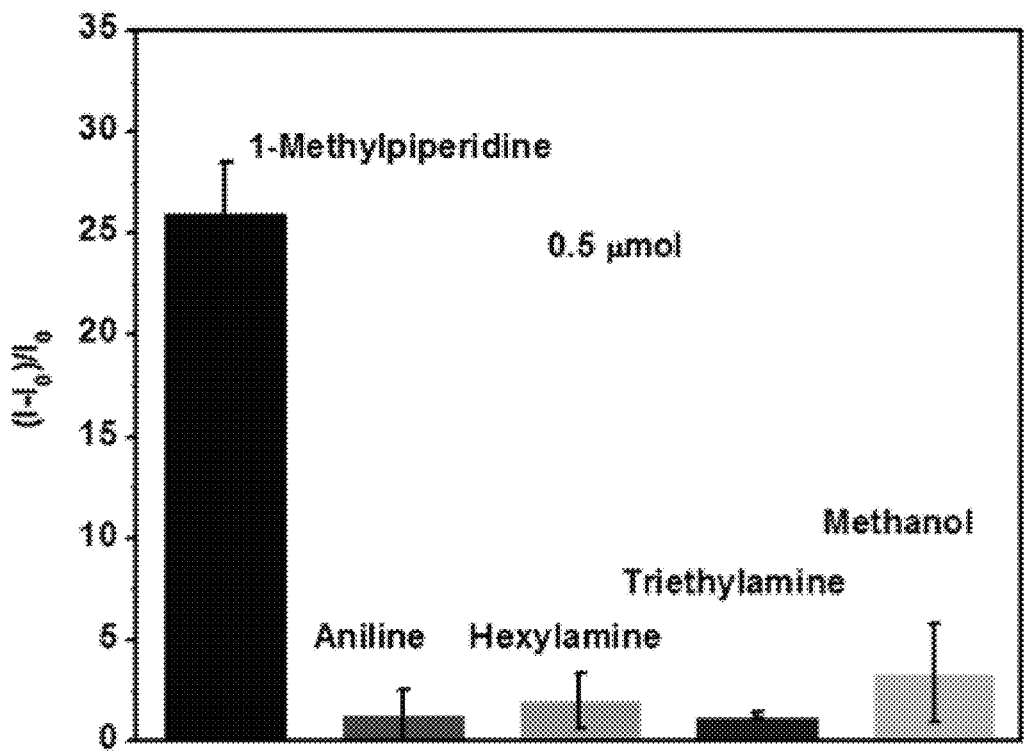
FIG. 9A is a histogram of current enhancement ratio of CH-PTCDI nanobelts upon surface coating of 0.5 µmol of different amines (1-methylpiperidine, aniline, hexylamine, triethylamine), and methanol, which was used as the solvent for these amines, was also tested as the control.
Figure 9B:
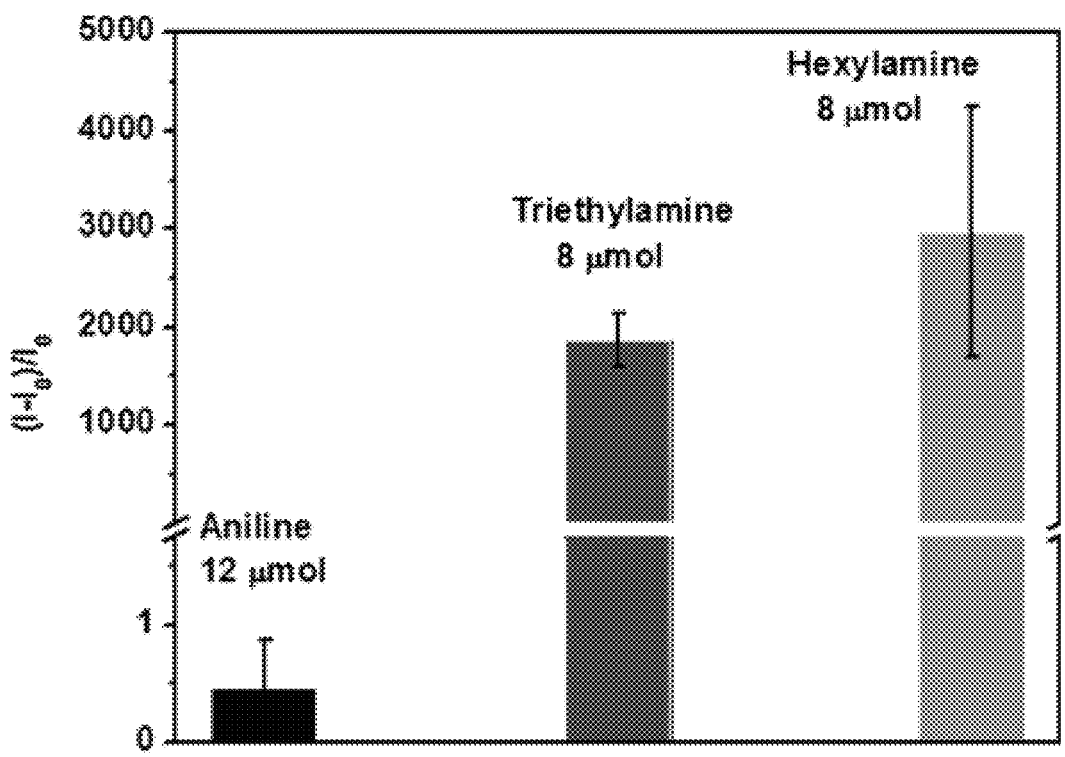
FIG. 9B is a histogram of current enhancement ratio of CH-PTCDI nanobelts upon surface-coating of much larger amount of amines (aniline 12 µmol, triethylamine 8 µmol, and hexylamine 8 µmol). All current values in histogram were gained at a bias voltage of 10 V.

To determine whether other amines can interact with PTCDI as strong as 1-methylpiperidine, aniline, hexylamine, and triethylamine were selected for comparative testing. Following the same experimental procedure of surface doping as described above, different amounts of amines were drop-cast onto the surface of the CH-PTCDI nanobelts. As shown in FIG. 9A, when 0.5 µmol of amine was applied, no obvious current enhancement was obtained by coating with aniline, hexylamine, and triethylamine, whereas a 26-fold increase in current was observed by coating with 1-methylpiperidine under the same conditions. However, a significant increase in current was observed when the amount of hexylamine and triethylamine increased to 8 µmol, for which the enhancement ratios were about 3000 and 1800, respectively (though still four orders of magnitude lower than 1-methylpiperidine), whereas aniline still produced negligible current even with as much as 12 µmol coated (FIG. 9B).

Figure 10A:
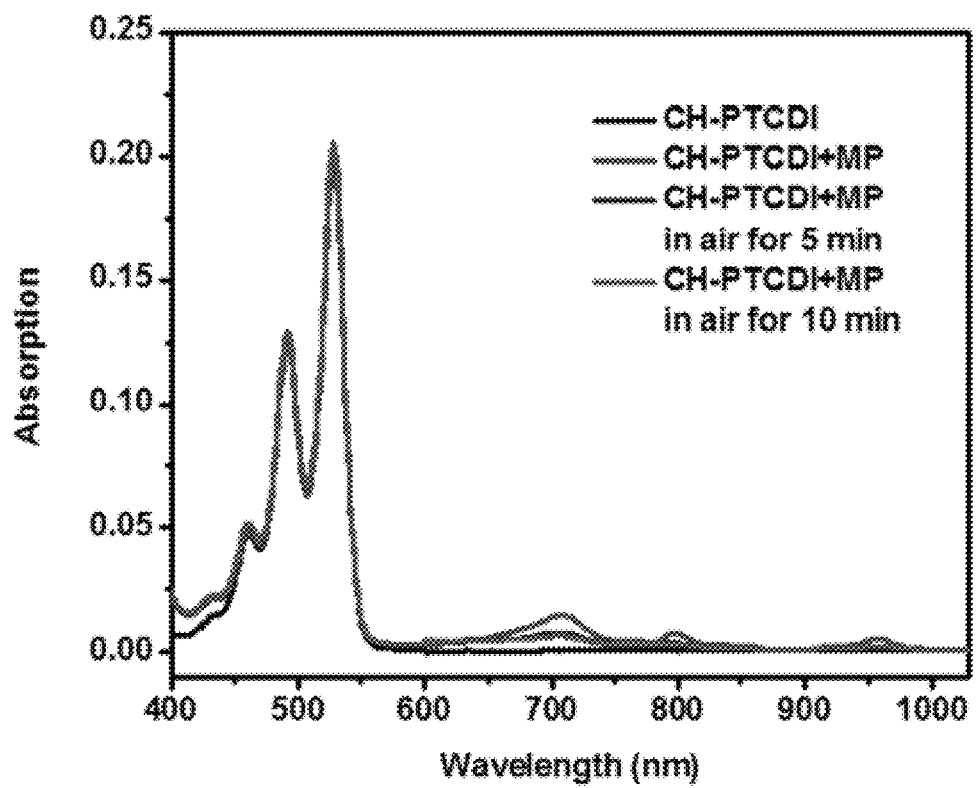
FIG. 10A is a depiction UV-Vis absorption spectra of deoxygenated DMSO solution of CH-PTCDI (10 µmol $L^{-1}$) before and after addition of excessive 1-methylpiperidine (MP, 0.1 mol $L^{-1}$), and the same solution after being exposed to air for 5 min and 10 min, respectively.
Figure 10B:
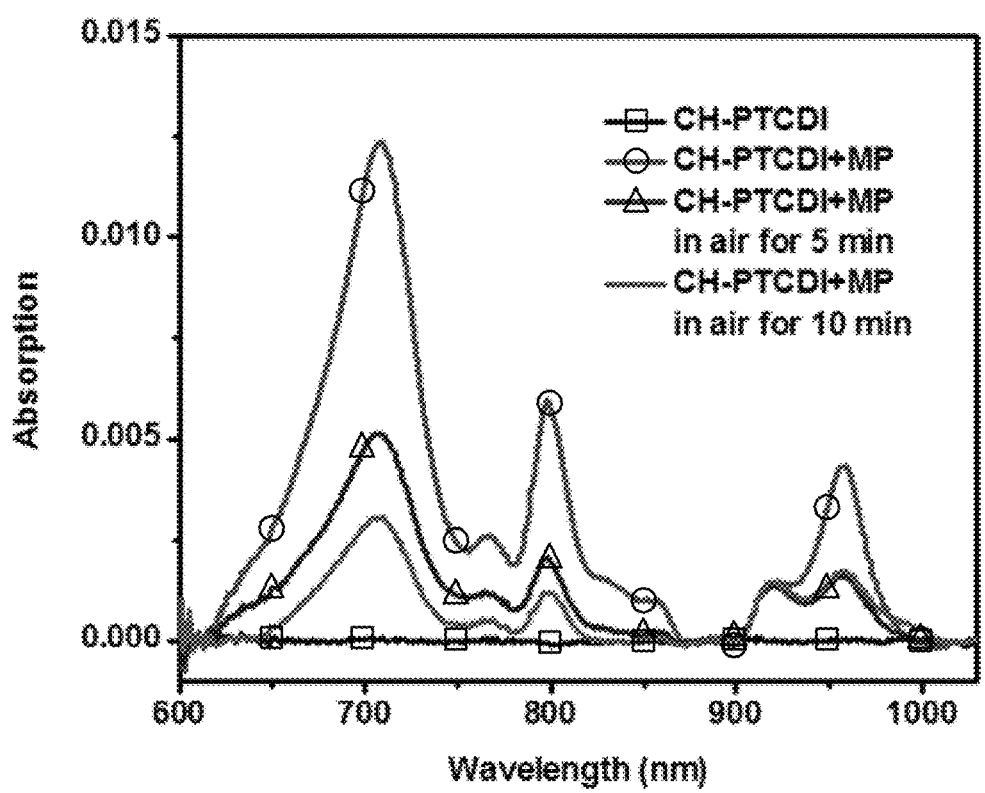
FIG. 10B is an Enlarged UV-Vis absorption spectra of FIG. 10A in the wavelength range of 600 nm to 1000 nm.
Figure 11A:
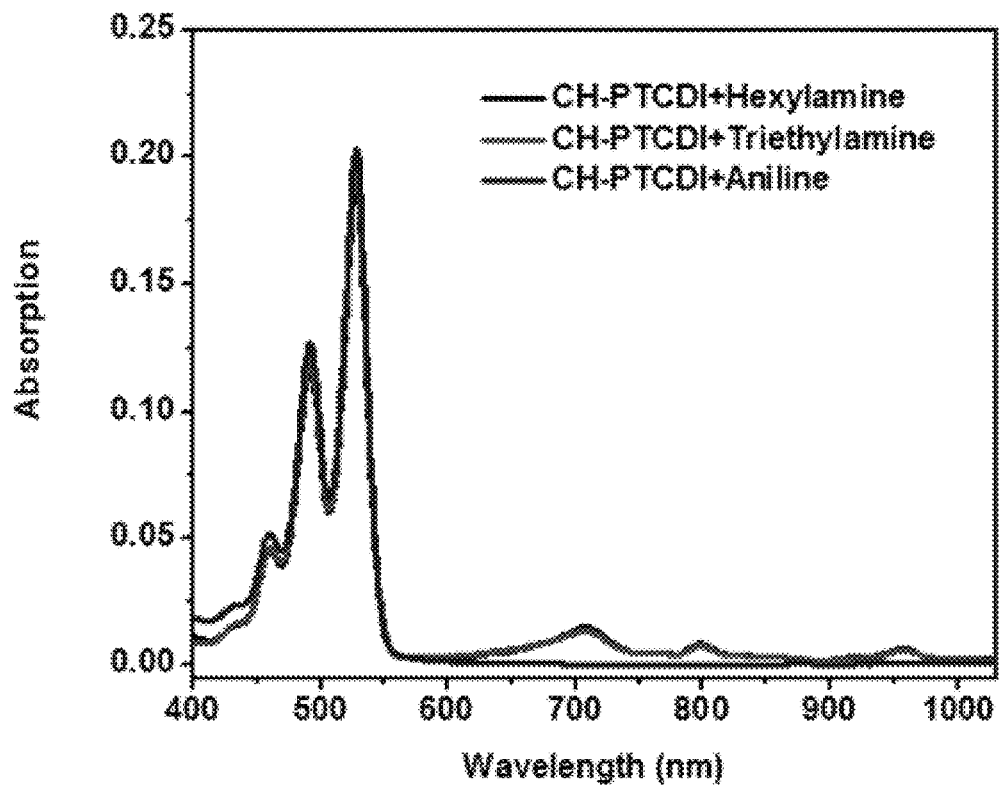
FIG. 11A is a UV-Vis absorption spectra of deoxygenated DMSO solution of CH-PTCDI (10 µmol $L^{-1}$) in the presence of excessive amine (0.1 mol $L^{-1}$) (hexylamine, triethylamine, aniline).
Figure 11B:
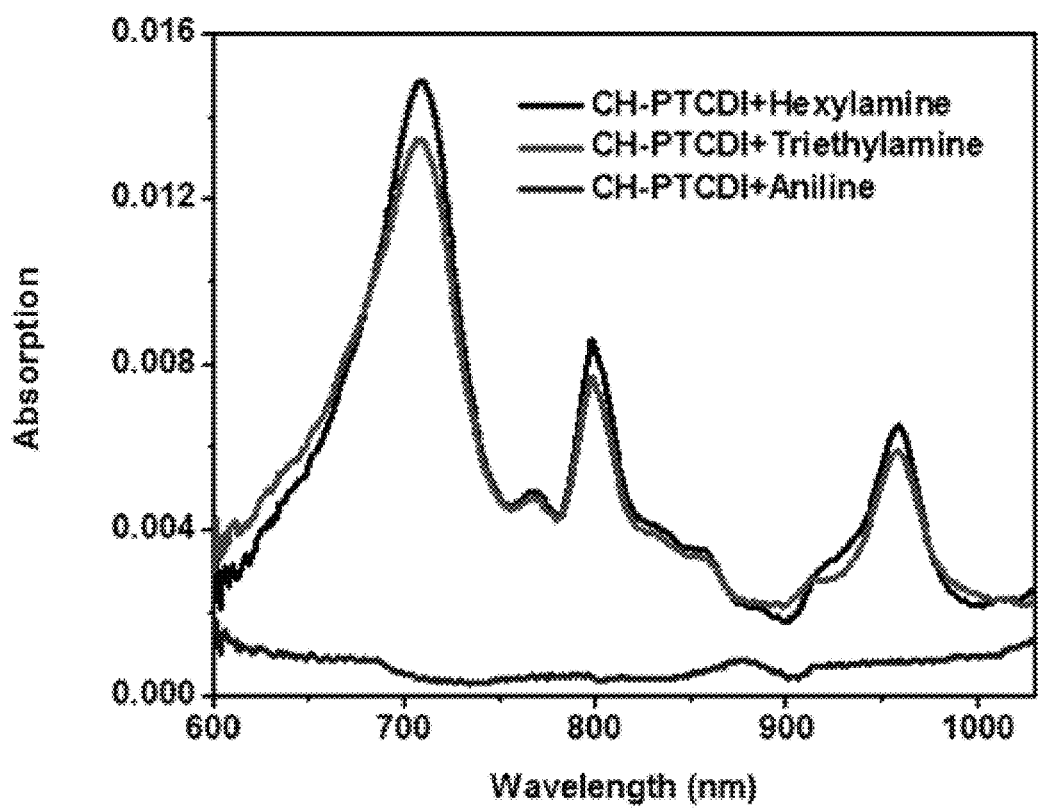
FIG. 11B is an enlarged UV-Vis absorption spectra of FIG. 11A in the wavelength range of 600 to 1000 nm.

Regarding the fact that the CH-PTCDI nanobelts coated by the three amines (1-methylpiperidine, hexylamine, and triethylamine) produced enhanced conductivity relative to the pristine CH-PTCDI nanobelts while those treated with aniline did not, the interaction between CH-PTCDI molecules and amines using UV-Vis absorption spectroscopy was studied. The PTCDI anionic radical upon adding the three amines into the oxygen free solution of CH-PTCDI in dimethyl sulfoxide (DMSO) was detected. The existence of three new absorption peaks at 708, 798, and 959 nm in the presence of 1-methylpiperidine indicated the formation of PTCDI anionic radicals (FIGS. 10A-B). In the absence of oxygen, the radicals are very stable. Upon exposure to air, the three characteristic peaks diminish with time, which further confirms the formation of oxygen-sensitive PTCDI anionic radicals. Moreover, analysis based on the redox potentials suggests that the electron transfer from 1-methylpiperidine to PTCDI is a thermodynamic favorable (spontaneous) process. In addition to 1-methylpiperidine, PTCDI anionic radicals were also generated by addition of hexylamine and triethylamine (FIGS. 11A-B). However, no such anionic radicals were generated upon addition of aniline to the same deoxygenated solution of CH-PTCDI (FIGS. 11A-B). This comparative observation is consistent with the above discussed results of conductivity enhancement upon casting of different amines, indicating that the effective charge transfer interaction (and thus generating PTCDI anionic radical) is the primary cause of the conductivity enhancement. The electrons thus generated can delocalize (migrate) along the π-π stacking of PTCDIs, acting as the major charge carrier for the n-type material.

The electron donating strength of amines can be evaluated by the oxidation potentials. The selection rule of donor relies on a thermodynamics analysis, i.e., the Gibbs free energy change ($\Delta G$) of the electron transfer process forming the anionic radical must be negative, $\Delta G<0$. The Gibbs free energy change ($\Delta G$) of the electron transfer can be calculated from the redox potentials of species under certain concentrations; $\Delta G$ thus obtained will indicate whether the electron transfer is a thermodynamically favorable (spontaneous) process, for which $\Delta G<0$. The oxidation potential of 1-methylpiperidine (MP) is 1.08 V vs SCE (i.e., saturated calomel electrode), and the reduction potential of PTCDI is 0.658 V vs SCE (Note: the electronic property (redox potential) of PTCDI does not change significantly with the different side groups since the two imide positions are nodes in the 7c-conjugation). For example, the starting concentration of PTCDI and MP used in our solution phase UV-vis spectral measurement were 10 µmol/L and 0.1 mol/L, respectively. When the redox reaction reached its equilibrium as shown in FIGS. 10A and 10B, the concentration of PTCDI anionic radical can be estimated to be about $1 \times 10^{-7}$ mol/L, according to Beer-Lambert law (given the molar absorption coefficient of PTCDI anionic radical is $\epsilon=36000$ L/mol $cm^{-1}$ at 956 nm, peak absorbance=0.0039 at that wavelength, optical length=1 cm). The concentration of the counterpart (cationic ion) MP⁺ should be the same as that of the PTCDI anionic radical, $1\times10^{-7}$ mol/L. So, from the Nernst equation XX, and T=293 K, the electrical potential ($\Delta E$) of the redox (electron transfer) reaction between MP and PTCDI can be calculated (below) to be 0.042 V, which gives a negative $\Delta G$, meaning a spontaneous process for the electron transfer in the solution phase.

$$\Delta E = \Delta E^0 - \frac{RT}{zF}\ln\frac{[PTCDI^-][D^+]}{[PTCDI][D]} \qquad (XX)$$

$$\Delta G = -zEF \qquad (XXI)$$

where R is the universal gas constant, z is the number of electrons transferred per ion pair, F is the Faraday constant, [D] is the concentration of donor group, [D⁺] is the concentration of the donor cationic ion, [PTCDI] is the concentration of PTCDI, and $\Delta E^0$ is the electric potential difference of the PTCDI and donor groups. Considering the tight intermolecular packing within MP-PTCDI nanoribbons (pi-pi stacking distance between PTCDI planes is about 3.5 Å), the local concentration of MP and PTCDI in the solid would be much higher than that in the solution phase. Therefore, the Gibbs free energy change ($\Delta G$) of the electron transfer should be increased (becoming more negative), meaning the generation of PTCDI anionic radicals should be more favored in the nanoribbons. So for the donors without experimental data, it is expected that whenever the electrical potential ($\Delta E$) of the electron transfer reaction between donor and PTCDI in the molecular assembly (at certain concentration) is positive, meaning the $\Delta G$ is negative, the donor group would satisfy the criteria for self-doping to donate an electron into PTCDI.

Among all the amines used, aniline would be the strongest electron donor from their oxidation potentials (1-methylpiperidine, $E^\circ_{ox}$=1.08 V vs SCE; hexylamine, $E^\circ_{ox}$=1.44 V vs SCE; triethylamine, $E^\circ_{ox}$=0.99 V vs SCE; aniline, $E^\circ_{ox}$=0.86 V vs SCE). However, as evidenced by these results, no charge transfer was observed between aniline and PTCDI even in the presence of a large excess of aniline (i.e., no significant current enhancement was observed with 12 μmol aniline coated on the CH-PTCDI nanobelts, and no absorption peaks of PTCDI anionic radical were detected in the deoxygenated DMSO solution of CH-PTCDI (10 μmol/L) in the presence of excessive aniline (0.1 mol/L)). The lack of charge transfer between aniline and PTCDI might be due to the weak nucleophilicity of aniline, which prevents the strong donor-acceptor interaction.

Figure 13B:
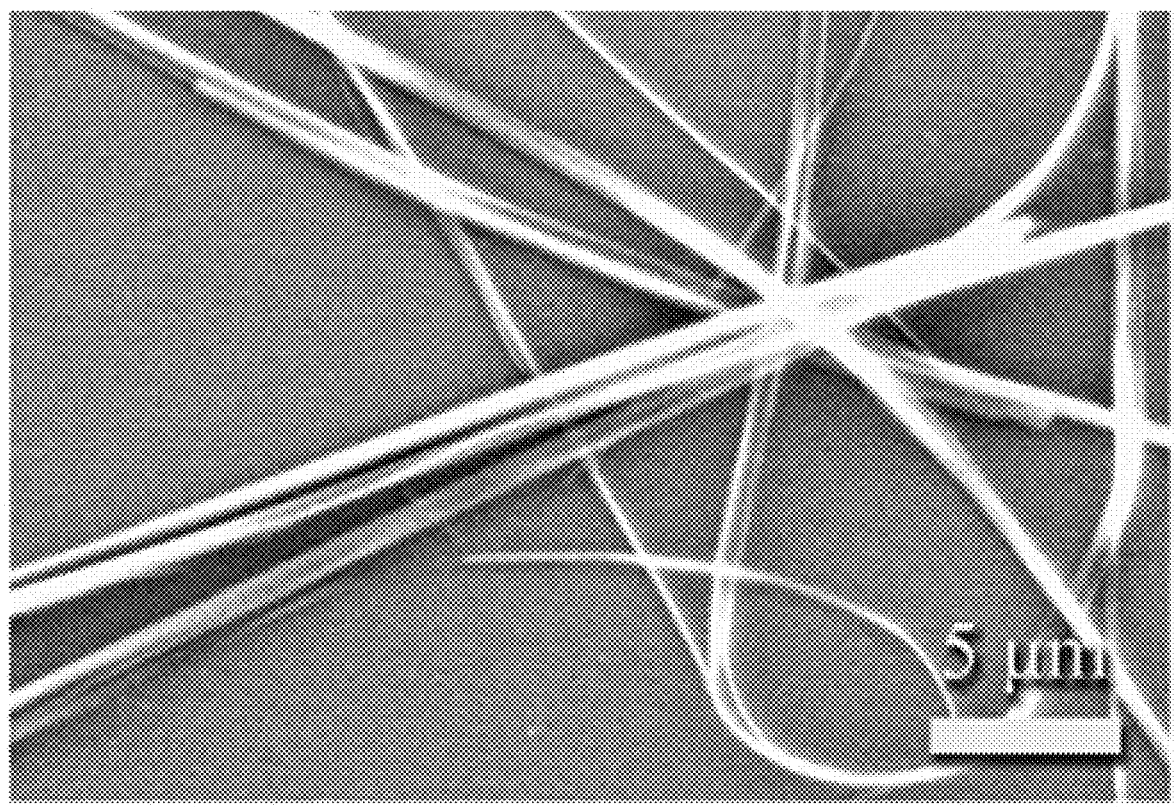
FIGS. 13B-13C are SEM images of the CH-PTCDI nanobelts before (13B) and after (13C) surface coating with 1-methylpiperidine.
Figure 13C:
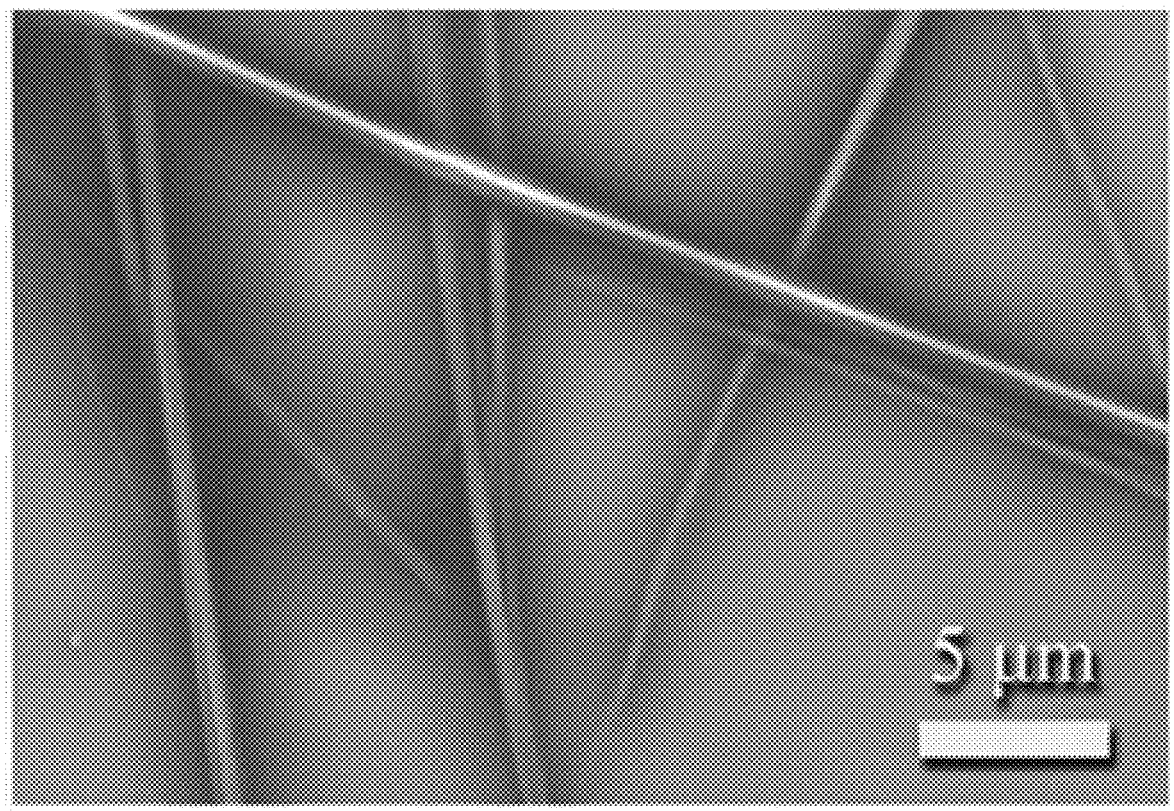

On the basis of the aforementioned results and discussion, an n-type doping mechanism, which is a result of the generation of PTCDI anionic radicals, explains the high conductivity of the MP-PTCDI nanoribbons. As demonstrated in FIG. 1, upon self-assembly into nanoribbons, the side-groups of 1-methylpiperidine are in close proximity of the PTCDI backbones, enabling charge transfer interaction to form PTCDI anionic radicals (the reduction of PTCDI by 1-methylpiperidine can be more thermodynamically favored in solid state compared to solution phase due to a much higher local concentration in solid). Owing to the efficient intramolecular π-electron delocalization within the PTCDI plane, the electron (anionic radical) generated can be well stabilized (against charge recombination) as observed in the UV-Vis absorption spectral measurement (FIGS. 11A-11B). When this occurs inside the nanoribbons, the electron can effectively survive scavenging by oxygen, making the high conductivity gained sustainable even in the ambient environment as indeed observed in this study (FIGS. 13A-13C). With an applied bias, the self-doped electrons rapidly migrate along the long axis of the nanoribbon facilitated by the intermolecular π-π electron delocalization, leading to the high conductivity. The resultant PTCDI anionic radical is an n-type dopant in which the substitutional dopant is a zwitterionic molecule, a PTCDI anionic radical linked to an amine centered cation (a reduced analogue of the PTCDI host molecule). An n-doped PTCDI film was fabricated by spin-coating mixed PTCDI dopant and host materials solution, resulting in ten orders of magnitude of increase in conductivity with just 1% doping.

The morphology of the CH-PTCDI nanobelts before and after surface coating remained unchanged as characterized by SEM (FIG. 13B, 13C). Interestingly, the built up surface charging on the pristine CH-PTCDI nanobelts was eliminated by surface coating with 1-methylpiperidine. The SEM image of pristine CH-PTCDI nanobelts shows bright imaging contrast on the surface of the nanobelts, which is a characteristic of the surface charge built up on the nonconductive sample after E-beam exposure during SEM measurement (FIG. 13B). However, such surface charging was suppressed after surface coating of the 1-methylpiperidine (FIG. 13C). This phenomenon is common in SEM measurements performed on nonconductive samples, for which a thin layer of metal, such as Au, Pt, or Pd, is typically deposited on the sample surface to facilitate charge transmission and prevent charge building up. Since the pure 1-methylpiperidine film is not overly conductive (FIG. 6C), the observed conductivity improvement should be due to the charge transfer interaction between 1-methylpiperidine and CH-PTCDI nanobelts, consistent with the current enhancement discussed above.

Chemiresistive Sensing for Hydrogen Peroxide Vapor Detection.

Figure 14:
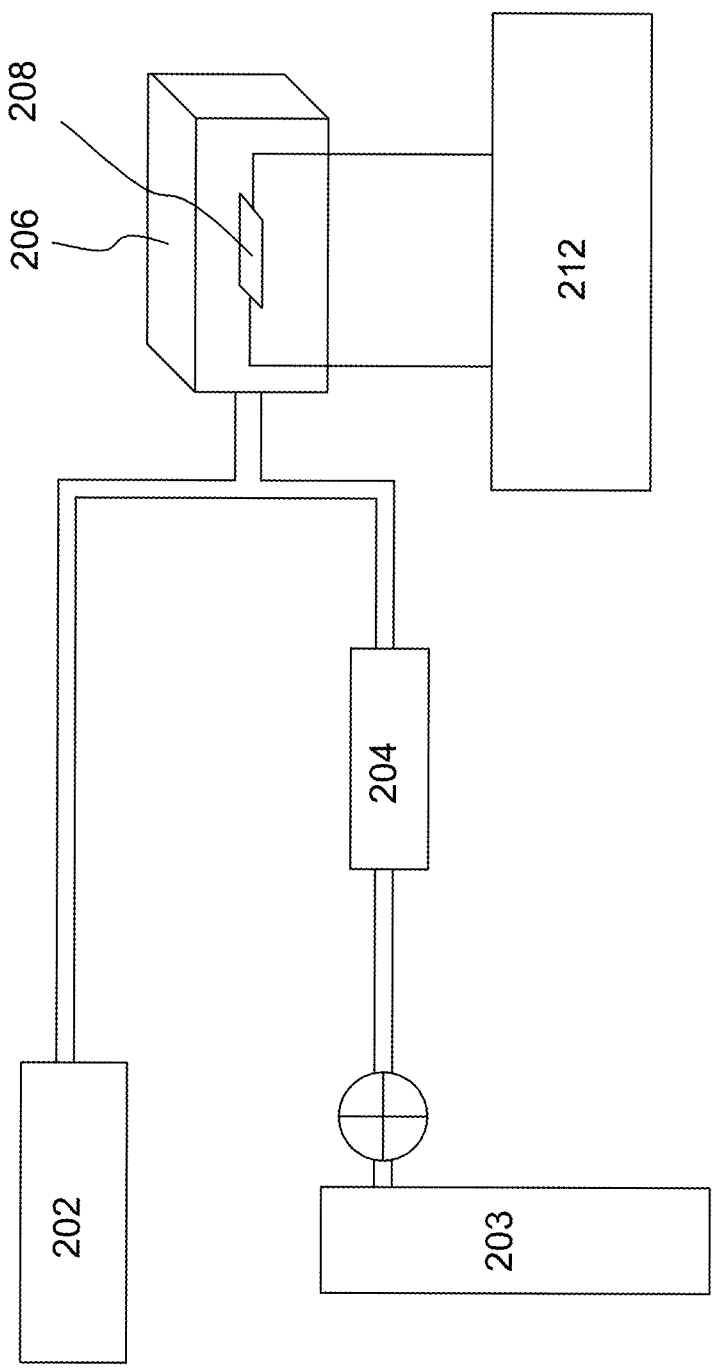
FIG. 14 is a schematic diagram of a vapor sensing measurement system, in accordance with some examples of the present disclosure.

All chemical vapor sensing tests were conducted under ambient conditions in the dark. FIG. 14 depicts a sensing and chemical vapor delivery system. A chemical vapor was pulled into a 50 mL syringe and delivered by syringe pump 202 (NE-4000 New Era Pump System, Inc.) at a rate of 25 mL/min into the carrier gas. The carrier gas was dry air delivered by a carrier gas container 203 and mass flow controller 204 at a flow rate of 475 mL/min. The final concentration of chemical vapor in the testing chamber 206 was calculated from the syringe volume and the concentration of original chemical vapor. The original $H_2O_2$ vapor was generated from 44.7 wt. % $H_2O_2$ solution (Sigma-Aldrich, 50 wt. % in $H_2O$). The IDE chip 208 (deposited with PTCDI nanomaterials) was placed on a ceramic chip carrier connected by wire bonding. The ceramic chip carrier was fixed on a breadboard, enclosed in a small Teflon chamber (3.84 cm in length, 1.86 cm in width, and 2.41 cm in height), and connected to an Agilent 4156C Semiconductor Analyzer 212. A bias of 10 V was applied across the electrodes and the current through the sensor was monitored. For $H_2O_2$ testing, the chip was exposed to $H_2O_2$ vapor for 30 s with a recovery time of 2.5 min. For testing toward the common liquid samples, the exposure time was 30 s with a recovery time of 30 s. The sensing response time of MP-PTCDI nanoribbons was obtained by fitting the time-course current change profile to an exponential function, which gives the response time as 1/e of the time constant obtained.

Figure 15:
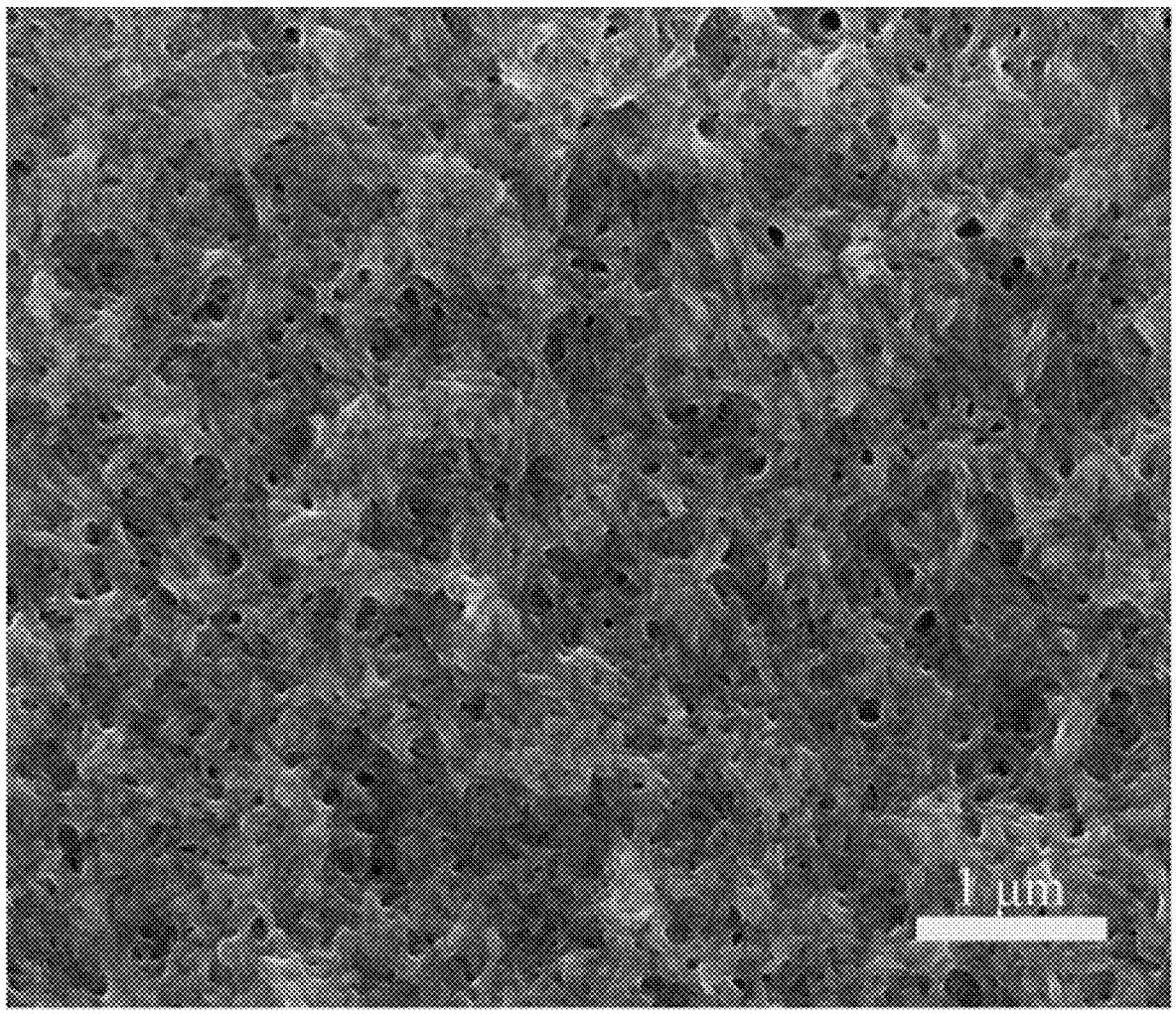
FIG. 15 is a SEM image of a porous MP-PTCDI nanoribbons film, formed by intertwined nanoribbons when drop-cast on a silicon substrate coated with 300 nm $SiO_2$ layer.

With the increased electrical conductivity by self-doping, MP-PTCDI nanoribbons can be a building material for chemiresistive sensors, for which the high conductivity improves the signal-to-noise ratio and simplifies the system design. A chemiresistive sensor based on the nanoribbons benefits from the large surface area and continuous porosity formed by the interlaced nanoribbons deposited on the substrate (FIG. 15). Combination of these two features enhances the adsorption and diffusion (accumulation) of gas analytes, thus increasing the sensing sensitivity. The n-type character of the PTCDI material allows for chemiresistive sensing of electron deficient analytes, which can be bound to the surface, causing charge depletion of the material. $H_2O_2$ vapor was chosen as the target analyte because it is a critical signature for the peroxide explosives including both the synthetic ones (e.g., TATP, DADP and HMTD) and the simple liquid mixtures of $H_2O_2$ and the fuels.

Figure 12:
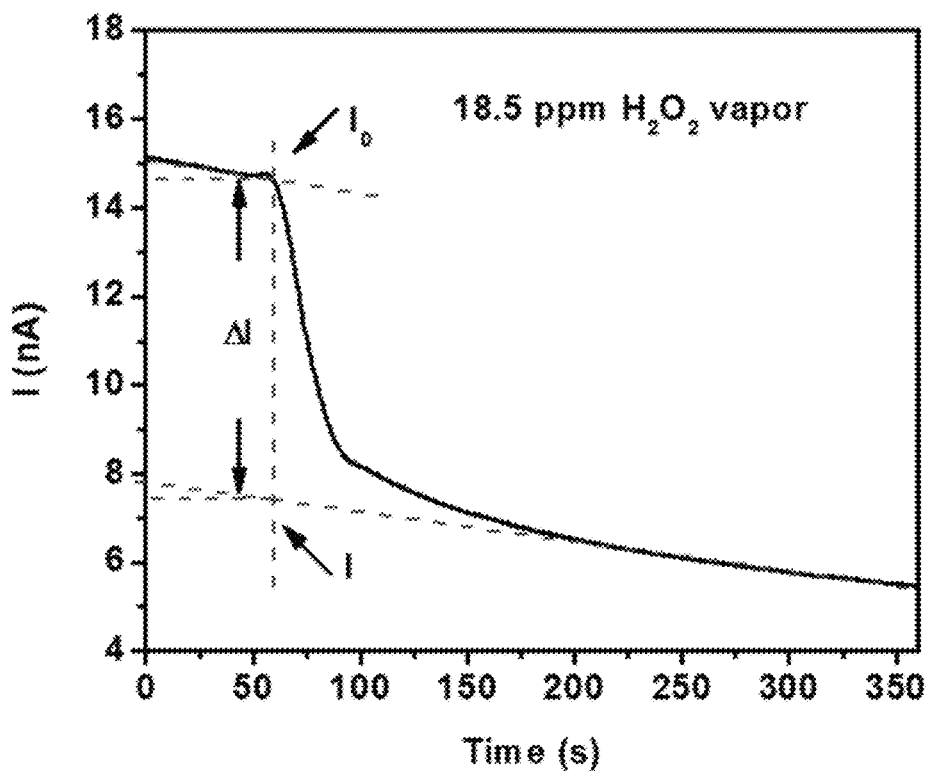
FIG. 12 is a plot demonstrating how to calculate the current decrease of MP-PTCDI nanoribbons in response to $H_2O_2$ vapor.
Figure 16A:
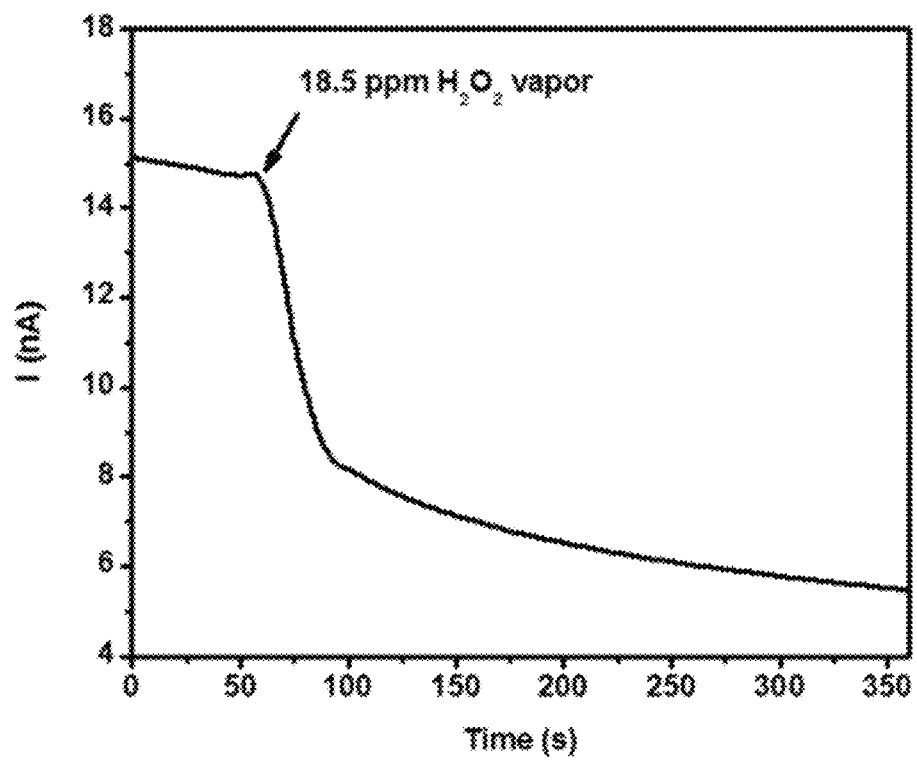
FIG. 16A is current measured over the MP-PTCDI nanoribbons in response to $H_2O_2$ vapor (18.5 ppm).
Figure 16B:
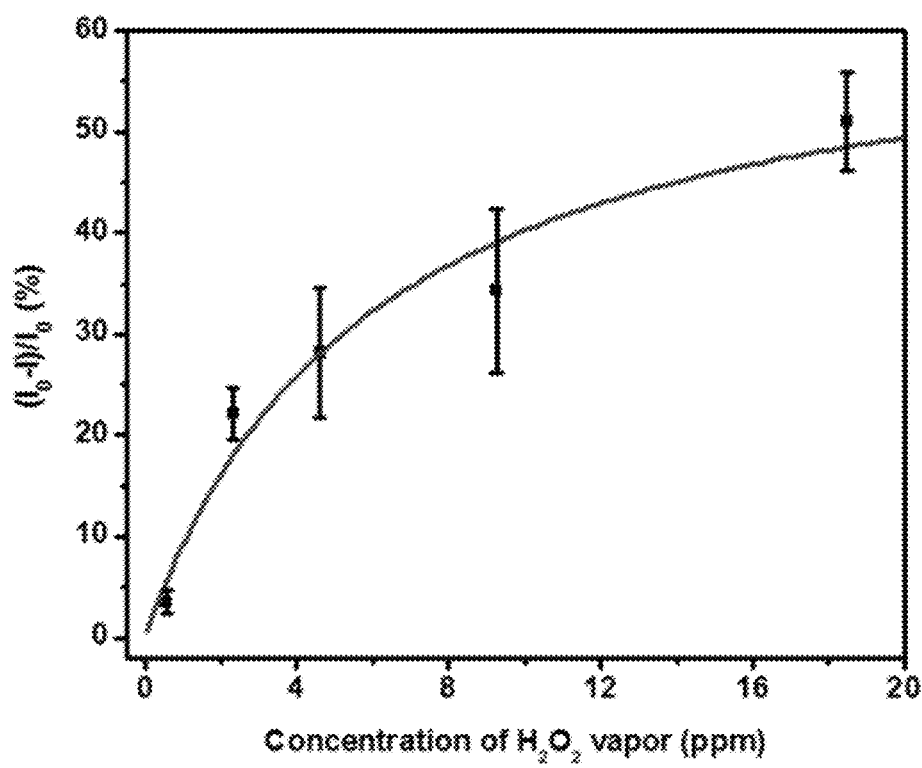
FIG. 16B is relative current change $[(I_0-I)/I_0\ (\%)]$ as a function of the concentration of $H_2O_2$ vapor, where I and $I_0$ are the current measured before and after exposure to $H_2O_2$ vapor, respectively.

FIGS. 12 and 16A show the real-time electrical current profile of an MP-PTCDI nanoribbon chemiresistor sensor in response to $H_2O_2$ vapor. Upon exposure to $H_2O_2$ vapor (18.5 ppm), there is an instantaneous decrease in current of about 50%. A very short response time of 19.5 seconds is attributed to the large surface area of the nanoribbons and expedient diffusion of $H_2O_2$ vapor. The response is concentration dependent. FIG. 16B shows a plot of relative sensor response as a function of the concentration of $H_2O_2$ vapor, which can be fit well into the Langmuir absorption model. The lowest concentration of $H_2O_2$ vapor that was tested in this study was 0.6 ppm, which represents the lowest level that can be provided by the present experimental setup. Nonetheless, the limit of detection of $H_2O_2$ vapor can be projected to be 200 ppb following the Langmuir adsorption model. The irreversible sensor response towards $H_2O_2$ is attributed to the strong surface binding of $H_2O_2$ and the permanent oxidation of 1-methylpiperidine groups by $H_2O_2$ ($E°red=1.78$ V, vs SCE).

Figure 17A:
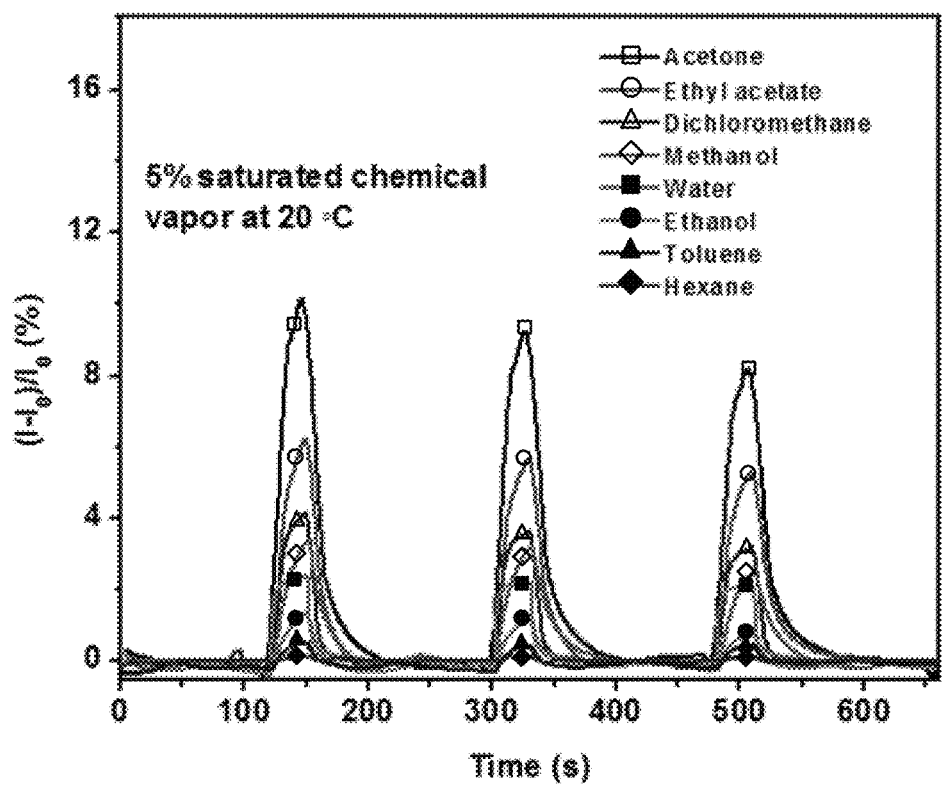
FIG. 17A is the relative current change $((I-I_0)/I_0)$ of MP-PTCDI nanoribbons in three subsequent exposures toward some common organic liquids and water at 5% of the saturated vapor concentration.
Figure 17B:
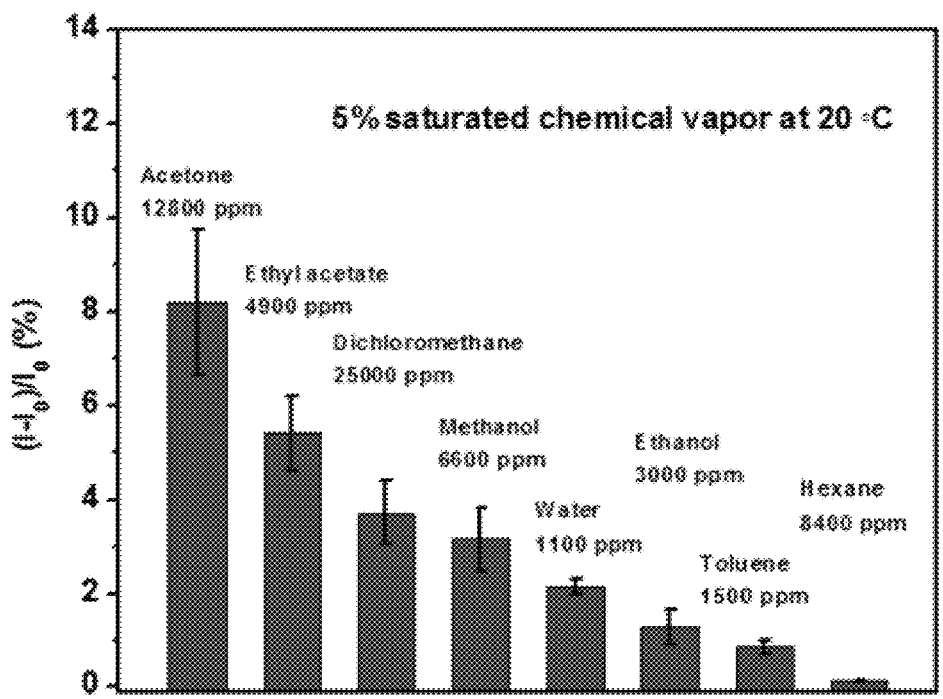
FIG. 17B indicates average values of $(I-I_0)/I_0$ measured over the MP-PTCDI nanoribbons when exposed to the different liquid vapors at 5% saturated vapor concentration.

In addition to the high sensitivity, the MP-PTCDI nanoribbons also demonstrated high selectivity towards $H_2O_2$ vapor against water and some common organic liquids, facilitating the development into practical sensing applications. Such general selectivity was investigated by measuring the sensor response toward the vapor of various common liquids, including water, acetone, ethyl acetate, dichloromethane, methanol, ethanol, toluene, and hexane. In contrast to the irreversible decrease response caused by $H_2O_2$ vapor, exposure to these liquids vapor resulted in reversible increase in current for the MP-PTCDI nanoribbons (FIGS. 17A-17B). The vapors exhibited fluorescence quenching (without photoexcitation) in increasing degree from lower to higher, respectively, with hexane, toluene, ethanol, water, methanol, dichloromethane, ethyl acetate and acetone as shown in FIG. 17A. The increased conductivity observed is likely a result of dipole interaction between MP-PTCDI nanoribbon and the liquid molecule. The sensing response and the dipole moment of the liquids appear to be tightly correlated. For liquids with smaller dipole moments, the response is lower. For example, the vapor concentration of hexane used (8400 ppm) is much higher than many other analytes, such as ethyl acetate (4900 ppm), water (1100 ppm), ethanol (3000 ppm), toluene (1500 ppm), but the relative response is only 0.1%, the lowest among all chemicals studied here, because the dipole moment of hexane is less than 0.1 Debye, much lower than others.

In conclusion, the nanoribbons assembled from the 1-methylpiperidine substituted-PTCDI molecules possess extraordinarily high conductivity relative to other PTCDI-based nanostructures. The 1-methylpiperidine group plays a key role in the conductivity enhancement, as evidenced by systematic experiments and analysis of the interaction between a model PTCDI nanobelt and 1-methylpiperidine. Upon self-assembly into one-dimensional nanoribbons, the 1-methylpiperidine groups interact with the PTCDI core in stacking proximity to produce the PTCDI anionic radical, which acts as the n-type dopant in the PTCDI lattice. The doping process increases the charge carrier density within the PTCDI nanoribbons, and the one-dimensional π-π stacking of PTCDIs is efficient for long range charge migration, thereby resulting in high conductivity. The high conductivity obtained supports application in chemiresistive sensors. The PTCDI nanoribbons demonstrated highly sensitive response to $H_2O_2$ vapor through oxidation, rather than dipole moment interaction as in the case of common liquid vapor, thereby producing general selectivity toward $H_2O_2$ vapor. Owing to the high conductivity of MP-PTCDI nanoribbons, as well as the porous mesh-like morphology of the nanoribbon film, the lowest detected concentration of $H_2O_2$ vapor in this study was down to 0.6 ppm, and the limit of detection is projected to be as low as 200 ppb.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A chemiresistive vapor sensor compound for detecting target vapors, comprising a perylene-tetracarboxylic diimide (PTCDI) core, wherein the compound has a structure according to structure I:

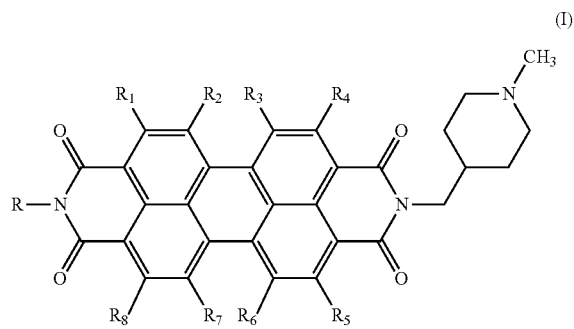

where R is a group that does not comprise 1-methylpiperidine, wherein the 1-methylpiperidine group of the compound transfers an electron directly to a PTCDI core of an adjacent molecule of the compound, without photo-excitation and while dry and at room temperature, sufficient to form an anionic PTCDI radical of the PTCDI core of the adjacent molecule, and R1 to R8 are independently side groups or hydrogen.

2. The chemiresistive sensor compound of claim 1, wherein R is a straight $C_2$-$C_{15}$ alkyl chain or a branched $C_8$-$C_{50}$ alkyl group.

3. The chemiresistive vapor sensor compound of claim 1, wherein the Gibbs free energy change for formation of the anionic PTCDI radical is less than zero.

4. The chemiresistive vapor sensor compound of claim 1, wherein R1-R8 are independently hydrogen, or $C_1$-$C_8$ alkyl groups.

5. A chemiresistive vapor sensor for detection of a target compound, the sensor comprising:

a. an assembly of nanofibers formed of a chemiresistive vapor sensor compound for detecting target vapors, comprising a perylene-tetracarboxylic diimide (PTCDI) core, wherein the compound has a structure according to structure I:

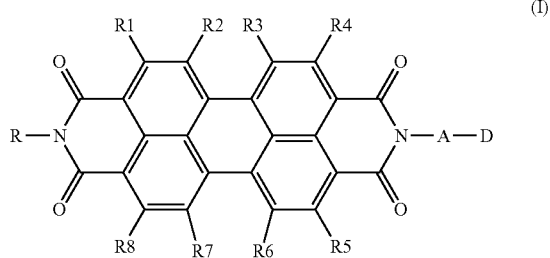

where R is a group that is different from A-D, A is a linking groups, D is a strong electron donor which transfers an electron directly from the strong electron donor to a PTCDI core of an adjacent molecule of the compound, without photo-excitation and while dry and at room temperature, sufficient to form an anionic PTCDI radical of the PTCDI core of the adjacent molecule, and R1 to R8 are independently side groups or hydrogen, and wherein A-D comprises

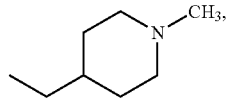

forming 1-methylpiperidine-substituted perylene tetracarboxylic diimide (MP-PTCDI); and b. a pair of electrodes operatively oriented about the assembly of nanofibers to allow electrical current to pass from a first electrode in the pair of electrodes through the assembly of nanofibers and to a second electrode in the pair of electrodes.

* * * * *